(12) United States Patent
Sumi

(10) Patent No.: US 6,677,143 B2
(45) Date of Patent: Jan. 13, 2004

(54) METHOD FOR CULTURING *BACILLUS SUBTILIS* NATTO TO PRODUCE WATER-SOLUBLE VITAMIN K AND FOOD PRODUCT, BEVERAGE, OR FEED CONTAINING THE CULTURED MICROORGANISM OR THE VITAMIN K DERIVATIVE

(75) Inventor: Hiroyuki Sumi, Okayama-ken (JP)

(73) Assignee: Honda Trading Company, Tokyo (JP)

( * ) Notice: Subject to any disclaimer, the term of this patent is extended or adjusted under 35 U.S.C. 154(b) by 0 days.

(21) Appl. No.: 09/907,290

(22) Filed: Jul. 17, 2001

(65) Prior Publication Data

US 2002/0001832 A1 Jan. 3, 2002

Related U.S. Application Data

(62) Division of application No. 09/317,072, filed on May 17, 1999.

(51) Int. Cl.$^7$ .................................................. C12P 7/66
(52) U.S. Cl. ............... 435/133; 435/252.5; 424/93.462; 424/442; 426/61
(58) Field of Search .............................. 435/252.5, 133; 424/93.462, 442; 426/61

(56) References Cited

U.S. PATENT DOCUMENTS

| | | | | |
|---|---|---|---|---|
| 4,919,936 A | * | 4/1990 | Iwanami et al. | ............ 424/442 |
| 6,096,719 A | * | 8/2000 | Matsutani et al. | ....... 435/172.1 |

FOREIGN PATENT DOCUMENTS

| | | |
|---|---|---|
| JP | B-07-028748 | 9/1987 |
| JP | B-07-051070 | 4/1988 |
| JP | A-08-009916 | 1/1996 |
| JP | A-08-019378 | 1/1996 |
| JP | A-08-073396 | 3/1996 |
| JP | A-08-173078 | 7/1996 |
| JP | A-10-295393 | 11/1998 |
| JP | A-11-032787 | 2/1999 |

OTHER PUBLICATIONS

Farrand et al., J. Bacteriol., 117:324–326 (1974).*
Ikeda et al., Eur. J. Biochem., 192:219–223 (1990).*
Sumi, H., Hamada, H., Tsushima, H., Mihara, H., and Muraki, H. "A novel fibrinolytic enzyme (nattokinase) in the vegetable cheese Natto; a typical and popular soybean food in the Japanese diet." Experientia, vol. 43, No. 10, pp. 1110–1111, Oct. 15, 1987.
Sumi, H., Hamada, H., Nakanishi, K., Hiratani, H. "Enhancement of the Fibrinolytic Activity in Plasma by Oral Administration of Nattokinase." Acta Haematologica, 1990, 84: pp. 139–143.
Sumi, H., Taya, N., Nakajima, N., Hiratani, H. "Structure and Fibrinolytic properties of Nattokinase" Fibronolysis, International Journal of Fibrinolysis, Thrombolysis and Extracellular Proteolysis, vol. 6, Supplement 2, 1992.
Sumi, H., Handa, O., Imamura, M. Kawasaki, S. "Kinetics of Vitamins (K1, MK–r, MK–7) after ingestion of Natto and Phylloquinone food in blood." Japanese Journal of Thrombosis and Hemostasis, vol. 8, No. 4, Aug. 1997, p. 287.
Sumi, H., Yatagi C., Kozaki Y. "Menaquinone types of Vitamin K (Menaquinone types of Vitamin K (MK–4 and MK–7) increased after ingestion of phylloquinone foods." Fibrinolysis & Proteolysis, vol. 12, Suppl. 1, Jun. 1998, p. 75.
Sumi, H. Accumulation of Vitamin K (Menaquinone–7) in plasma after ingestion of Natto and Natto Bacilli (*B. subtilis* natto). Food Science and Technology Research, vol. 5, No. 1, Feb. 1999, pp. 48–50.
Sumi, H., Yanagisawa, Y., Kozakim Y. "Production and Vitamin K (Menaquinone–y) by fermentation of okara and functions thereof." Nippon Nogeikagaku Kaishi, vol. 72, Special Issue, Mar. 5, 1998, p. 128.
Sumi, H. Yatagai, C., Kishimoto, N., Takaoka, S. "Study of Natto and *Bacillus subtilis* natto as Vitamin K (MK–7) preparation." Nippon Shokuhin Kagaku Kougakukai, Summary of 45$^{th}$ Lecture Meeting, Jul. 31, 1998.
Sumi, H. "Production of Nattokinase and Vitamin K by okara fermentation." Summer Study Meeting for Resource Use, Aug. 7, 1997.
Sumi, H., Yanagisawa, Y., Yoshida, E., Sumi, A. "A new functional feed KNP–001 as Nattokinase and Vitamin K (MK–7) agents." Clinical Pharmacology and Therapy, vol. 8, No. 6, pp. 631–635, Nov. 1998.
Sumi, H., Yanagisawa, Y., Kishimoto, N., Mori, R. "Study on *Bacillus subtilis* natto for Vitamin K." Nippon Nogeikagaku Kaishi, vol. 73, Special Issue, p. 138, Mar. 5, 1999.
Sumi, H., Yanagisawa, Y., Yatagai, C., Kozakim Y. "Production by fermentation of water–soluble Vitamin K and effects by ingestion thereof." Summary of 53$^{rd}$ Nippon Eiyo Shokuryo Gakkai Taikai, p. 133, Apr. 20, 1999.

(List continued on next page.)

*Primary Examiner*—Irene Marx
(74) *Attorney, Agent, or Firm*—Butzel Long

(57) ABSTRACT

A method for culturing *Bacillus subtilis* in such a manner that a vitamin K derivative is accumulated in the largest amount in the cells of the microorganism. A method for the culture of *Bacillus subtilis*, which comprises culturing *Bacillus subtilis* and recovering the cells of the microorganism before the vitamin K produced within the cells of the microorganism is released from the cells is disclosed, as well as the cultured product of *Bacillus subtilis* cultured by this method, a water-soluble vitamin K derivative originating in the cultured product, a food product, beverage, or feed containing the cultured product and/or the water-soluble vitamin K derivative, and a method for extracting vitamin K.

10 Claims, 8 Drawing Sheets

OTHER PUBLICATIONS

Sumi, H. "Production of fibrinolytic enzyme and Vitamin K by okara fermentation." Bioactive, No. 4, pp. 25–26, Feb. 3, 1999.

Sumi, H. "Determination of the Vitamin K (Menaquinone–7) content in fermented soybean Natto and in the plasma of Natto–ingesting subjects." Journal of Home Economics of Japan, vol. 50, No. 4, pp. 309–312, 1999.

Sumi, H., Yanagisawa, Y., Kishimoto, N., Mori, R. "Study on *Bacillus subtilis* natto for Vitamin K." Publication at Nippon Nogeikagakuklai In Fukuoka, Mar. 31, 1999.

Takata, et al., Pharm. Res. (1995), 12(12), 1973–9.

* cited by examiner

METHOD FOR CULTURING *BACILLUS SUBTILIS* NATTO TO PRODUCE WATER-SOLUBLE VITAMIN K AND FOOD PRODUCT, BEVERAGE, OR FEED CONTAINING THE CULTURED MICROORGANISM OR THE VITAMIN K DERIVATIVE

RELATED APPLICATION

This is a Divisional of U.S. patent application Ser. No. 09/317,072, filed on May 17, 1999.

BACKGROUND OF THE INVENTION

FIELD OF THE INVENTION

This invention relates to a method for culturing *Bacillus subtilis*, the cultured microorganism obtained by the method, a water-soluble vitamin K derivative originating in the cultured microorganism, and a food product, beverage, or feed containing the cultured microorganism or the water-soluble vitamin K derivative. More particularly, this invention relates to a method for culturing *Bacillus subtilis* in such a manner as to induce storage of a vitamin K derivative, particularly a menaquinone-7 (vitamin $K_2$) derivative, in the largest amount within the cells of the *Bacillus subtilis*, a cultured product of *Bacillus subtilis* having a vitamin K derivative, particularly a menaquinone-7 (vitamin $K_2$) derivative, accumulated in a large amount within the cells thereof in consequence of the culture by the method mentioned above, a water-soluble vitamin K derivative, particularly a water-soluble menaquinone-7 (vitamin $K_2$) derivative, originating in the cultured product mentioned above, and a food product, beverage, or feed containing the cultured product or the water-soluble vitamin K derivative, particularly the water-soluble menaquinone-7 (vitamin $K_2$) derivative.

DESCRIPTION OF THE RELATED ART

Vitamin K has been heretofore known as a factor found necessary during the coagulation of blood. Since the deficiency of this vitamin brings deterioration of the ability to coagulate blood, vitamin K is held to constitute itself one species of fat-soluble vitamin otherwise called an antihemorrhagic vitamin. As regards the cause for the deterioration of ability to coagulate blood thus brought about by the deficiency in this vitamin K, it has been suggested in recent years that vitamin K is indispensable for the biosynthesis of several blood coagulation factors including prothrombin. The amount of the vitamin K which is found necessary for the purpose of preventing the deterioration of the blood-coagulating ability is extremely small, i.e. on the order of $\mu$g. Generally, since adults are supplied with this vitamin K by enterobacteria, they rarely contract the disease of vitamin K deficiency. The synthetic vitamins $K_1$ and $K_2$ are used as medicines for the therapy of the disease of the vitamin K deficiency hemorrhage. To date, the vitamin K has not attracted much attention because the concentrate of natural vitamin $K_1$ has been utilized heretofore in the form of a food product for the purpose of preventing this disease.

It has been demonstrated in recent years, however, that vitamin K has a function of promoting ossification and a function of repressing bone resorption and that the density of bone is increased by the administration of the vitamin K. The osteoporosis is the pathosis of embrittlement of bone caused by senility or illness. Since this disease accompanies fracture and severe pain, it has been posing a serious social issue from the standpoint of geriatric therapy. A study conducted on patients with osteoporosis to determine their vitamin K levels in blood has demonstrated that the vitamin K levels average about one half of those of healthy persons. As a prospective medicine for the treatment of osteoporosis, therefore, the synthetic vitamin K is now under a clinical test. It has been established by the clinical test that in the treatment and prevention of osteoporosis, unlike the case of treating and preventing hemorrhage, the administration of vitamin K in such a large daily dose of not less than 45 mg is effective in increasing the amount of bone. The osteoporosis favors the prevention thereof rather than the treatment to be effected after the onset of the disease. For the sake of this prevention, daily ingestion of the vitamin K from food is commendable. The ingestion of the vitamin K in the dose mentioned above from the existing food seems to be difficult, however, because the question how much of the vitamin K ought to be ingested daily to increase the amount of bone and attain the prevention of osteoporosis remains yet to be elucidated.

The ingestion of vitamin K is preferred to be attained by the daily food as described above. In fact, vitamin $K_1$ can be taken from greenish yellow vegetables and marine plants and vitamin $K_2$ from such fermented food products as fermented soybeans (natto). An effort to attain the ingestion of 45 mg of the vitamin K, i.e. an amount reported to be effective in improving osteoporosis, from the commercially available food product, however, actually turns out to be a very difficult task as aptly evinced by the fact that a food product containing 1 ppm of vitamin K, for example, ought to be consumed in such a large amount as 45 kg daily to fulfill the ingestion under discussion. It is natto, among other food products, that has the largest vitamin K content on the order of ten-odd ppm. Even the natto so renowned ought to be consumed in such a large amount as some hundreds of g to several kg daily to fulfill the ingestion. From the standpoint of taste, it is difficult for any person to form the habit of eating the natto in such a large amount as mentioned above daily. In addition to this difficulty, the ingested vitamin K has a short half-life period. The vitamin K has such unsolved problems as failing to manifest the effect thereof fully satisfactory when it is orally ingested independently and tending to entail adverse reactions when it is ingested in an unduly large amount all at once. While the ingestion of the vitamin K in the concentrated form is commendable, the commercially available natural vitamin K concentrate which additionally incorporates therein prepared milk powder for the sake of preventing hemorrhage is expensive and the synthetic vitamin K offered as a pharmaceutical preparation is not usable as food.

Incidentally, in the class of vitamin K's, it are only the vitamin $K_1$ and $K_2$ groups that occur in nature. The vitamin $K_1$ is copiously contained particularly in green vegetables, vegetable oils, and marine products among other kinds of food. Seaweed, laver, and tea leaves, for example, contain some tens of ppm of vitamin $K_1$ and soybean oil, spinach, and broccoli, for example, contain several ppm of vitamin $K_1$. This vitamin $K_1$ is synthesized by condensing 2-methyl-1,4-naphthoquinone and phytyl acetate. Further, the vitamin $K_2$ group is known as varying homologs of menaquinone-1 to -14 (MK-1 to MK-14), depending on the difference in chain length. Among other homologs, particularly the menaquinone-7 (occasionally referred to simply as "MIK-7" in the present specification) is a typical substance of the vitamin $K_2$ and is synthesized mainly by *Bacillus subtilis* natto. In nature, the MK-7 is isolated only with unusual difficulty because it occurs in a relatively minute amount in the range of several to ten-odd ppm even in natto and has a short half-life period. So far, the invention of JP-A-08-73,396 has been known as the sole case of succeeding in preparing a lipid having a high MK-7 content.

Thus, quantity production of vitamin $K_2$ by the use of such a microorganism as *Bacillus subtilis* natto has been attempted. Many studies have been known to have perfected methods for producing natural vitamin $K_2$. Methods for collecting vitamin $K_2$ from the culture broth of a microorganism belonging to genus Flavobacterium (JP-B-07-28,748 and JP-B-07-51,070) and methods for producing vitamin K by inoculating *Bacillus subtilis* natto to soy beam soup stock or soy-bean cake lees and fermenting the microorganism in the medium (JP-A-10-295,393, JP-A-08-19,378, JP-A-08-9,916, and JP-A-08-173,078) may be cited as examples of the outcomes of such studies. In addition to these methods, a method for obtaining a concentrated lipid containing natural vitamin $K_2$, particularly natural MK-7, in a large amount by subjecting the fermented cells of *Bacillus subtilis* natto to extraction with such an organic solvent as alcohol, ether, ester, or ketone has been proposed (JP-A-08-73,396). The methods which use such a vitamin K-producing microorganism as Flavobacterium have the problem that the vitamin $K_2$ obtained thereby can not be utilized in its unmodified form for a food product because the safety of Flavobacterium as food has not been established. Though the methods which prepare the vitamin K by the use of *Bacillus subtilis* natto indeed obtain cultures with relatively high vitamin K contents reaching the maximum of about 40 mg/litter of culture broth, the products thereof find utility only in heavily restricted applications because they are not water-soluble but fat-soluble bulks of vitamin K. Further, the lipid with a high natural menacruinone-7 content prepared by extracting the fermented cells of *Bacillus subtilis* natto with an organic solvent, despite the use of such raw materials as soy beans which are available for food, uses the organic solvent and, therefore, requires thorough removal of the organic solvent before it is used in food. This removal of the organic solvent necessitates provision of a special device intended exclusively therefor and entails an addition to the time required for the operation. The lipid of high MK-7 content to be obtained is a fat-soluble product, similarly to the products mentioned above, as clearly inferred from the designation thereof and, consequently, finds utility only in limited applications.

Many methods for producing vitamin K and MK-7 by using such microorganisms as *Bacillus subtilis* natto from the fermented broths of natto and such by-products as lees generated during the course of manufacture of natto and soup stock (namely for extracting vitamin K and MK-7 from the cells of the microorganism) have been reported in literature. Virtually no reports have been heretofore made concerning vitamin K and MK-7 stored within the cells of species of *Bacillus subtilis* represented by *Bacillus subtilis* natto.

An object of this invention, therefore, is to provide a method for culturing *Bacillus subtilis* in such a manner as to induce storage of a vitamin K derivative, particularly a menaquinone-7 (vitamin $K_2$) derivative, in the largest amount within the cells of the *Bacillus subtilis*, a cultured product of *Bacillus subtilis* having a vitamin K derivative, particularly a menaquinone-7 (vitamin $K_2$) derivative, accumulated in a large amount within the cells thereof in consequence of the culture by the method mentioned above, a water-soluble vitamin K derivative, particularly a water-soluble menaquinone-7 (vitamin $K_2$) derivative, originating in the cultured product mentioned above, and a food product, beverage, or feed containing the cultured product mentioned above or the water-soluble vitamin K derivative, particularly the water-soluble menaquinone-7 (vitamin $K_2$) derivative.

Another object of this invention, directed at rendering natural vitamin K, particularly natural MX-7, which either cannot be ingested at all or may be ingested only with difficulty, in a sufficient amount from the ordinary food product ingestible easily and daily, is to provide a method for culturing *Bacillus subtilis* in such a manner as to induce storage of a vitamin K derivative, particularly a menaquinone-7 (vitamin $K_2$) derivative, in the largest amount within the cells of the *Bacillus subtilis*, a cultured product of *Bacillus subtilis* having a vitamin K derivative, particularly amenaquinone-7 (vitamin $K_2$) derivative, accumulated in a large amount within the cells thereof in consequence of the culture by the method mentioned above, a water-soluble vitamin K derivative, particularly a water-soluble menaquinone-7 (vitamin $K_2$) derivative, originating in the cultured product mentioned above, and a food product, beverage, or feed containing the cultured product mentioned above or the water-soluble vitamin K derivative, particularly the water-soluble menaquinone-7 (vitamin $K_2$) derivative.

Still another object of this invention, directed at rendering natural vitamin K, particularly natural MK-7, which either cannot be ingested at all or may be ingested only with difficulty, in a sufficient amount from the ordinary food product ingestible easily and daily, is to provide a method for culturing *Bacillus subtilis* in such a manner as to induce storage of a vitamin K derivative, particularly a menaquinone-7 (vitamin $K_2$) derivative, in the largest amount within the cells of the *Bacillus subtilis*, a cultured product of *Bacillus subtilis* having a vitamin K derivative, particularly a menaquinone-7 (vitamin $K_2$) derivative, having effects of maintaining the level thereof in blood as heightened to a necessary level for a long time and at the same time excelling in safety accumulated in a large amount within the cells thereof in consequence of the culture by the method mentioned above, a water-soluble vitamin K derivative, particularly a water-soluble menaquinone-7 (vitamin $K_2$) derivative, originating in the cultured product mentioned above, and a food product, beverage, or feed containing the cultured product mentioned above or the water-soluble vitamin K derivative, particularly the water-soluble menaquinone-7 (vitamin $K_2$) derivative.

SUMMARY OF THE INVENTION

The present inventor, in appreciation of the true state of prior art mentioned above, has pursued a diligent study on the components of natto (Experientia, 43:1110, 1987; Acta Haematol., 84: 139, 1990; Fibrinolysis, 6: 86, 1992; Journal of Japan Society of Pharmacists, 30: 73, 1994; Bio-Industry, 14: 47, 1996) or the analysis of vitamin K in *Bacillus subtilis* natto and in blood (Japan Thrombotic Hemostasis Journal, 8: 287, 1997; Fibrinolysis & Proteolysis, Vol. 12, Supplement 1, 205, p. 75, 1998) and has consequently found that rather than the ingestion of the fermented product of *Bacillus subtilis* natto such as fermented soybeans or the vitamin K contained therein, the ingestion of live *Bacillus subtilis* itself is recognized to be highly effective in promoting the level of vitamin K, particularly MK-7, in plasma and that particularly the ingestion of *Bacillus subtilis* natto manifests effects of maintaining the level in plasma at an extremely high level as compared with the ingestion of other substances.

The present inventor has also found that *Bacillus subtilis* natto cultured to a specific stage of growth has MK-7 accumulated in a large amount in the cells thereof, that by ingesting the *Bacillus subtilis* natto or the fermented product thereof recovered at this stage, it is recognized to heighten the level of vitamin K, particularly MK-7, in plasma, and that the level of the vitamin K in plasma obtained in consequence of the ingestion is maintained for a long time. In addition to this knowledge, the inventor has also found that the vitamin K, particularly the MK-7, accumulated in the cells of *Bacillus subtilis* natto recovered at the stage mentioned above is soluble in water and has come to entertain expectations that applications of the water-soluble vitamin K, particularly MK-7, will greatly expand.

This invention has been perfected based on the knowledge as described above.

Specifically, the objects mentioned above can be accomplished by a method for culturing *Bacillus subtilis*, comprising the steps of culturing *Bacillus subtilis* and recovering the cells of said *Bacillus subtilis* before the vitamin K produced in the cells is released from the cells.

The objects mentioned above can be further accomplished by a cultured product of *Bacillus subtilis* obtained by the culturing method of this invention, a water-soluble vitamin K derivative originating in the cultured product of *Bacillus subtilis*, and a food product, beverage, or feed containing the fermented product mentioned above and/or the water-soluble vitamin K derivative.

The method for culturing *Bacillus subtilis* according to this invention is characterized by culturing *Bacillus subtilis* and recovering the cells of the *Bacillus subtilis* before the vitamin K produced in the cells is released from the cells. By the method of this invention, therefore, the *Bacillus subtilis* used therein can be recovered in a state having the vitamin K derivative, particular the menaquinone-7 derivative, stored in the largest amount within the cells thereof. For this reason, the water-soluble vitamin K, particularly the menaquinone-7 derivative, can be recovered in a larger amount from the cultured product as compared with the conventional method. Further, particularly when *Bacillus subtilis* natto is used, since the safety thereof has been ensured, the cultured product obtained by the method mentioned above or the food product, beverage, or feed containing the water-soluble vitamin K derivative originating in the cultured product contains the water-soluble vitamin K derivative, particularly the menaquinone-7 derivative, in a larger amount and possesses higher safety as compared with the conventional product. The practice of eating this food product, beverage, or feed can be expected to ensure efficiently simple daily ingestion of vitamin K and advance further the improvement of osteoporosis.

The water-soluble vitamin K derivative originating in the cultured product obtained by the method of the present invention embraces an epochal invention purporting that the vitamin K heretofore obtained in a fat-soluble form can be converted into a water-soluble quality. Further, the water-soluble vitamin K derivative has excellent photostability. This particular invention can be expected not only to enlarge appreciably the use found for the new vitamin K as compared with the conventional fat-soluble vitamin K but also to confer a very high value on this invention from the industrial point of view.

Further, since the practice of ingesting the food product, beverage, or feed containing the cultured product or the water-soluble vitamin K derivative can be expected to allow more effective prevention of osteoporosis because it permits the level of vitamin K in plasma to be efficiently heightened and enables the heightened level in plasma to last for a far longer period than the vitamin K assimilated from conventional medicines or food products.

The above and other objects, features and advantages of the present invention will become clear from the following description of the preferred embodiments.

DETAILED DESCRIPTION OF THE PREFERRED EMBODIMENT(S)

Figure 1:
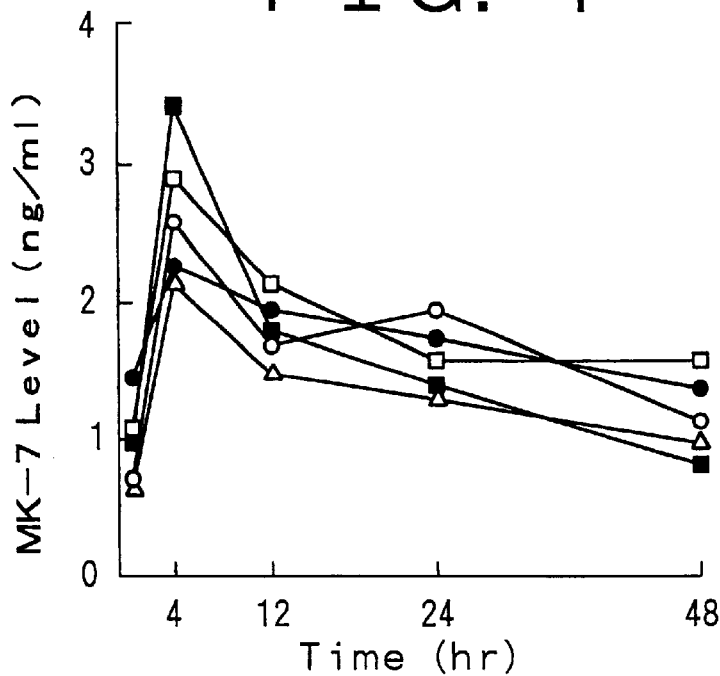
FIG. 1 is a graph showing time-course changes in levels of vitamin K (menaquinone-7) in plasma of five healthy adults each having orally ingested a dose of 1 g of dry *Bacillus subtilis* natto prepared in Example 1.

This invention will be described in detail below.

According to the first aspect, this invention provides a method for culturing *Bacillus subtilis*, which comprises culturing *Bacillus subtilis* and recovering the cells of said *Bacillus subtilis* before the vitamin K produced in the cells is released from the cells.

The *Bacillus subtilis* to be used in this invention does not need to impose any restriction particularly but requires only to belong to genus *Bacillus subtilis* and possess the ability to produce vitamin K. Any of the known species of genus *Bacillus subtilis* can be used. Particularly in consideration of such factors as safety and amount of vitamin K to be produced, *Bacillus subtilis* natto may be preferably used in this invention. *Bacillus subtilis* natto preferably used in this invention does not need to impose any restriction particularly. As typical examples thereof, such commercially available species of *Bacillus subtilis* natto as Takahashi strain (made by Yuzo Takahashi Laboratory in Yamagata), Naruse strain (made by Naruse Fermentation Chemical Laboratory K.K. in Tokyo), Miyagino strain (made by Miyagino Natto Manufactory K.K. in Sendai), Asahi strain (made by Asahi Kogyo K.K. in Tokyo), Nitto strain (made by Nitto Yakuhin Kogyo K.K. in Kyoto), and Meguro strain (made by Meguro Laboratory K.K. in Osaka) and Unnan SL-001 strain may be cited. In consideration of the amount of vitamin K derivative to be accumulated in the cells, Meguro strain, Miyagino strain, Takahashi strain, Naruse strain, Asahi strain, Nitto strain, and Unnan SL-001 strain may be used in the order of decreasing preferability (the amounts of vitamin K derivative produced increase in this order). Incidentally, Unnan SL-001 strain was internationally deposited under FERM BP-6713 at the National Institute Bioscience and Human-Technology Agency of Industrial Science and Technology on May 7, 1999.

In this invention, it is essential that the culture of *Bacillus subtilis* be terminated before the vitamin K produced in the microorganic cells is released from the cells and the vitamin K be recovered from the cells. For the culture of *Bacillus subtilis* as contemplated by this invention (with respect to composition of culture medium and culture conditions), the same composition of culture medium and culture conditions as are generally employed in the culture of any species of *Bacillus subtilis* can be used. Since this culture permits selective and copious accumulation of the vitamin K in the microorganic cells without being released in any appreciable amount from the cells, the cells containing the vitamin K in a large amount therein may be obtained by a simple procedure of recovering the cells in the specific state mentioned above. The cells thus recovered, particularly when the microorganism has the safety thereof established as in the case of *Bacillus subtilis* natto, can be used for the purpose of ingestion in the unmodified form without undergoing such an extra work as of extracting the vitamin K thereof, alternatively the cultured cells can be incorporated in an ordinary food product.

In this invention, the time for recovering the cells of *Bacillus subtilis* must precede the release of the produced vitamin K from the cells as mentioned above. Preferably, it may be the time at which the number of microorganic cells shifts from the logarithmic growth phase to the maximum stationary phase. Particularly when *Bacillus subtilis* is *Bacillus subtilis* natto, the recovery of the cells may be preferably made when the logarithmic growth phase is in the process of shifting to the maximum stationary phase and the production of nattokinase has not been started. More specifically, though the culturing time is variable with such culturing conditions as culturing temperature, pH, and initial concentration of cells and the culturing method as well, when Unnan SL-001 strain is inoculated at an initial concentration of $5 \times 10^6$/ml to 300 ml of a culture broth (containing 1.5% polypeptone-S, 1% glucose, and 0.1% yeast extract, pH 7.2) in an Erlenmeyer flask having an inner volume of 500 ml and shaking-cultured therein (100 rpm) at 37° C., for example, the time falls between 0.5 and four days and preferably occurs immediately after the absorbance at 660 nm reaches the maximum level (one to two days thereafter).

In this invention, for the culture of *Bacillus subtilis*, the same culture medium and culture conditions as are generally adopted for culturing any species of *Bacillus subtilis* maybe used. For example, the culture medium to be used for the culture which is contemplated by this invention does not need to be restricted particularly. Any of the culture media using such components as are well-known to persons skilled in the art can be used. A culture medium prepared by suitably mixing various culture components, a commercially available culture medium in its unmodified form, or a culture medium obtained by having the aforementioned known components additionally incorporated in the commercially available culture medium may be used. The culture medium thus used may be either a solid medium or a liquid medium, whichever better suits the purpose for which the medium is to be used. The culture medium is only required to contain a carbon source, a nitrogen source in a proper amount, an inorganic salt, and other nutrients which can be assimilated by the microorganism to be used, without reference to the choice between a synthetic medium and a natural medium.

The carbon source which can be used in the culture of *Bacillus subtilis* according to this invention is variable with the species of the microorganism to be used. It imposes no restriction particularly but requires only to allow the strain in use to grow satisfactorily and produce vitamin K with high efficiency. As typical examples of the carbon source, starch and compositional fractions thereof, roasted dextrin, processed starch, starch derivative, physically treated starch, α-starch, soluble starch, amylose, amylopectin, malt oligo sugar, oligosaccharide, cyclodextrin, pullulan, corn starch, potato starch, sweet potato starch and dextrin, glycerin, sorbitol, malt extract, and glucose and other similar carbohydrates may be cited. From the viewpoint of the production of vitamin K, glucose and starch may be preferably used among other carbon sources mentioned above. These carbon sources may be used either singly or in the form of a mixture of two or more members.

The nitrogen source to be used in the culture of *Bacillus subtilis* according to this invention is likewise variable with the species of the microorganism to be used. It imposes no restriction particularly but requires only to allow the strain in use to grow satisfactorily and produce vitamin K with high efficiency. As typical examples of the nitrogen source, meat extract, malt extract, peptone, polypeptone derived from soybean (such as, for example, polypeptone-S), yeast extract, tasty liquid (acid hydrolyzate of soybean starch), soybean powder, milk casein, Casamino acid, organic nitrogen compounds such as various amino acids and corn steep liquor, ammonia, ammonium salts such as ammonium nitrate, ammonium sulfate, and ammonium chloride, nitrates such as sodium nitrate, and inorganic nitrogen compounds such as urea may be cited. From the viewpoint of the production of vitamin K, polypeptone derived from soybean (such as, for example, polypeptone-S) and soybean powder are preferably used among other nitrogen sources mentioned above. These nitrogen sources can be used either singly or in the form of a mixture of two or more members.

The inorganic salt to be used in the culture of *Bacillus subtilis* according to this invention is likewise variable with the species of the microorganism to be used. It imposes no restriction particularly but requires only to allow the strain in use to grow satisfactorily and produce vitamin K with high efficiency. As typical examples of the inorganic salt, phosphates, hydrochlorides, sulfates, acetates, and etc. of magnesium, manganese, calcium, sodium, potassium, copper, iron, and zinc may be cited. These inorganic salts can be used either singly or in the form of a mixture of two or more members.

The commercially available culture media which can be used for the culture according to this invention include nutrient broth (dry bouillon) (produced by Nissui Seiyaku K.K. or Nippon Seiyaku K.K.) and polypeptone-S (made by Wako Pure Chemical Industries, Ltd.), for example.

Alternatively, in this invention, as the culture medium for use in the culture of *Bacillus subtilis* contemplated thereby, such materials as tofu (bean-curd) refuse, soybean, soybean soup stock by-produced during the manufacture of soybean paste and fermented soybeans (natto), soybean cake lees by-produced during the manufacture of soybean cake and deep-fried soybean cake, soybean cake lees by-produced during the manufacture of edible oil from soybean as the raw material, and soybean seed rind by-produced during the manufacture of soybean paste which can be fermented by

*Bacillus subtilis* natto can be used. In this case, the culture medium, when necessary, may suitably incorporate therein such carbon sources, nitrogen sources, and inorganic salts as mentioned above.

In this invention, the culture of *Bacillus subtilis* may be carried out in the same manner as in the method heretofore known in the art. The culture conditions used according to this invention can be properly selected to suit the microorganic strain, the composition of culture medium, and the method of culture to be adopted. They impose no restriction particularly but require only to allow the microorganic strain in use to propagate and produce vitamin K with high efficiency. The culturing temperature may be generally in the range of 20° to 45° C., preferably in the range of 37° to 42° C. and the pH value of the culture medium proper for the culture may be generally in the range of 6.0 to 9.5, preferably in the range of 7.0 to 8.5.

According to the second aspect, this invention provides the cultured product of *Bacillus subtilis* obtained by the method described above.

In this invention, the phrase "cultured product of *Bacillus subtilis*" may include both the cultured cell of *Bacillus subtilis* and the product yielded out the cell of *Bacillus subtilis*. In latter case, Unnan SL-001 strain may be preferably used because higher yield out the cell thereof.

According to the third aspect, this invention provides the water-soluble vitamin K derivative which originates in the cultured product according to the second aspect of this invention.

The cultured product of *Bacillus subtilis* obtained by the method of this invention may have a large amount of vitamin K, particularly vitamin $K_2$, and more particularly menaquinone-7 (MK-7), accumulated in the cells thereof as described above. Specifically, the amounts of vitamin K, vitamin $K_2$, and MK-7 accumulated in the cultured product of *Bacillus subtilis* according to the method of this invention, though variable with the used strain, the kind of a culture medium, and the culturing conditions to be adopted, generally fall each in the range of 10 to 200 mg/100 g of vacuum dried cells. More specifically, when Meguro strain is shaking-cultured (100 rpm) in a medium containing 3% of soybean peptone at 37° C. for two days, the maximum amount of MK-7 accumulated in the cells is about 70 mg/100 g of dry cells, which is equivalent to about 80 times the amount (870 $\mu$g/100 g) in the natto shown in the table of food product analysis published by Science and Technology Agency. Incidentally, the amounts of MK-7, MK-4, and vitamin K, accumulated in the microorganic cells indicated in the present specification are numerical values determined by the method which is described in detail as below.

When the cultured product of *Bacillus subtilis* produced by the method of this invention is collected by the known method such as filtration or centrifugal separation and then dried by the well-known method such as freeze drying, air drying, and vacuum heat drying and the dry cells are dissolved in water, the vitamin K is dissolved out in the water. From this fact in combination with the fact that the cells contain a large amount of vitamin K (particularly MK-7), it may be assumed that the vitamin K (particularly the MK-7) accumulated in the cells becomes water-soluble because it has undergone some sort of change in the cells. The vitamin K, vitamin $K_2$, and menaquinone-7 in the form thus endowed with this water-solubility will be referred to in the present specification as "water-soluble vitamin K derivative" (or simply as "vitamin K derivative"}, "water-soluble vitamin $K_2$ derivative" (or simply as "vitamin $K_2$ derivative"), and "water-soluble menaquinone-7" (or water-soluble MK-7 derivative) respectively. In view of the fact that the menaquinone-7 has a molecular weight of about 649 in combination with the fact that the water-soluble menaquinone-7 derivative exhibits a single band of a molecular weight of about 100,000 when measured by the SDS-polyacrylamide gel electrophoresis and a molecular weight of not less than 100,000 when measured by the gel filtration, it can be suspected that the water-soluble vitamin K derivative (inclusive of a vitamin $K_2$ derivative and a menaquinone-7 derivative; which stipulation will be omitted hereinafter) is present inside the cells in such a state that vitamin K including vitamin $K_2$ and menaquinone-7 binds a certain substance (such as, for example, glycopeptide) and stabilized. It goes without saying, however, that the postulate just mentioned will not limit the concept of this invention.

In this invention, the vitamin K derivative, vitamin $K_2$ derivative, and menaquinone-7 derivative have the solubility in water varied with the species of the microorganism, the kind of the culture medium to be used, the culturing conditions, the method for treating (extracting) the cultured product. For example, the water-solubility of the vitamin K derivative, in the case of extracting cultured cells with water, is about 150 $\mu$g/100 ml water (20° C.), in the case of the supernatant of the cultured medium, is about 300 $\mu$g/100 ml water (20° C.), and in the case of extracting cultured natto with water, is about 1,500 $\mu$g/100 ml water (20° C.).

According to the fourth aspect, this invention provides a food product, beverage, or feed containing the cultured product according to the second aspect and/or the water-soluble vitamin K derivative according to the third aspect as mentioned above.

The food product, beverage, or feed according to this invention, particularly when the microorganism to be used has the safety thereof established as in the case of *Bacillus subtilis* natto, may be composed solely of the cultured product according to the second aspect and/or the water-soluble vitamin K derivative according to the third aspect as mentioned above.

Alternatively, the food product, beverage, or feed according to this invention may have the cultured product according to the second aspect and/or the water-soluble vitamin K derivative according to the third aspect as mentioned above incorporated in a food product, beverage, or feed which can be normally consumed by eating. As typical examples of the food product, beverage, or feed intended for normal consumption by eating, bean curd refuse, fermented bean curd refuse, natto, soybean, soybean soup stock by-produced during the manufacture of soybean paste and fermented soybeans (natto), soybean curd lees by-produced during the manufacture of soybean curd (tofu) and deep-fried soybean curd, soybean lees by-produced during the manufacture of edible oil from soybean as the raw material, soybean seed rind by-produced during the manufacture of soybean paste, dairy products such as yogurt and cheese, kneaded marine products such as boiled fish paste, tube-shaped fish paste cake, cake of pounded fish, bar-shaped fish paste, and fish ball, processed seafood such as mashed and seasoned fish, processed meat products such as sausage, frankfurter, and lever paste, soybean products such as soybean curd (tofu), broiled soybean curd, fried bean curd, deep-fried soybean curd, fried bean curd cake having vegetables and other ingredients wrapped therein, bean curd refuse, freeze dried bean curd, and sheet of bean curd, processed vegetable products such as puree, processed potato products such as mashed potato, arrowroot starch, bean-starch vermicelli, konjak, and noodles made from devil's tongue starch, processed cereal products such as rice cake, rice-flour dumplings, boiled rice, breadlike food made of wheat gluten, rice vermicelli, macaroni, spaghetti, fine noodles, buckwheat noodles, noodles, Chinese noodles, instant noodle, loaf of bread, ship biscuit, and bun filled with bean jam, frozen food, nutritional supplementary food, sweeteners such as jam, oils and fats such as butter, margarine, mayonnaise, and dressing, confectionery products such as candy, molded dry cake, very small rice biscuits, sponge cake, sweet jellied adzuki-bean paste, bean-jam-filled wafers, bun filled with bean jam, soft rice cake filled with bean jam, dumpling, sweetened cake, chocolate, biscuit, cookies, doughnut, cakes, pies, ice cream, pudding, bavarois, and chewing gum, gel-like food products such as bean curd, jelly, konjak, agar, and gelidium jelly, marine plants such as kelp, seaweed, laver, and agar weed, and all the other food products; various fruit juices (orange, pineapple, apple, grape, melon, and strawberry), various bicarbonate beverages, tea (inclusive of green tea and oolong tea), drinking yoghurt, milk, soymilk, modified milk, mineral water, soft drink, coffee, black tea, cocoa, and all the other beverages; and feed for normally kept animals such as domestic animals like pig, cow, horse, sheep, and goat, pets such as dog, cat, rabbit, and hamster, and poultry and fish may be cited.

When the food product, beverage, or feed contains the cultured product according to this invention, the amount of the cultured product in the food product, though variable with the species of microorganism to be used, the kind of culture medium, the culturing conditions, and the content of water-soluble vitamin K derivative, is such that the food product generally contains 0.001 to 20% by weight of dry cells, preferably 0.1 to 5% by weight of dry cells, the beverage generally contains 0.0001 to 5 (w/v) % of dry cells, preferably 0.01 to 5 (w/v) % of dry cells, and the feed generally contains 0.0001 to 5% by weight of dry cells, preferably 0.001 to 1% by weight of dry cells. When the food product, beverage, or feed contains the water-soluble vitamin K derivative according to this invention, the amount of the water-soluble vitamin K derivative in the food product, though variable with the species of microorganism to be used, the kind of culture medium, and the culturing conditions similarly in the case mentioned above, is such that the food product generally contains 0.00001 to 10% by weight of water-soluble vitamin K derivative, preferably 0.0001 to 0.1% by weight of water-soluble vitamin K derivative, the beverage generally contains 0.00001 to 0.1 (w/v) % of water-soluble vitamin K derivative, preferably 0.0001 to 0.01 (w/v) % of water-soluble vitamin K derivative, and the feed generally contains 0.00001 to 10% by weight of water-soluble vitamin K derivative, preferably 0.0001 to 1% by weight of water-soluble vitamin K derivative.

By ingesting the food product, beverage, or feed containing the cultured cells containing the water-soluble vitamin K (particularly MK-7) derivative of this invention in a large amount and/or the water-soluble vitamin K (particularly MK-7) derivative originating in the cultured cells, therefore, the vitamin K, particularly the MK-7 can be taken efficiently in a large amount at a time without any undue stress (without entailing any undue discomfort) as compared with the conventional vitamin K. When the microorganism is *Bacillus subtilis* natto, this food product proves advantageous because of established safety.

According to the fifth aspect, this invention provides a method for extracting a vitamin K which comprises Soxhlet-extracting the cultured cells of *Bacillus subtilis*.

One embodiment of this aspect is described as below. Firstly, cultured microorganic cells are Soxhlet-extracted with such an organic solvent as hexane, diethylether, acetone, ethanol and isopropanol by using a Soxhlet extractor at a boiling temperature of the used solvent to obtain a fat-soluble fraction. Then, this fraction is extracted from such an organic solvent as hexane, diethylether, acetone, ethanol and isopropanol at 30° to 100° C. for 0.1 to 20 hours. The resultant extract is diluted with the same organic solvent as just used to a prescribed total volume. An aliquot of the diluted extract is intimately mixed with water and isopropanol and further mixed with the same organic solvent as just used as by the use of a touch mixer. The resultant liquid mixture is centrifuged and the supernatant is dried to hardness and the dry residue is dissolved in ethanol to prepare a fat-soluble vitamin K including vitamin $K_2$ (MK-7, MK-4), and vitamin $K_1$ having a higher purity.

By this method, a fat-soluble vitamin K can be extracted more efficiently as compared with the conventional methods and thus a fat-soluble vitamin K including vitamin $K_2$ (MK-7, MK-4), and vitamin $K_1$ can be recovered from the cultured cells with a higher yield.

According to sixth aspect, this invention provides a method for fractioning a water-soluble vitamin K derivative which comprises acidifying a culture medium of *Bacillus subtilis* to obtain a precipitate.

One embodiment of this aspect is described as below. *Bacillus subtilis* cells are cultured by a conventional method or the method as described above to obtain a culture medium. Then, the pH of this culture medium is decreased, preferably to a level in the range of 1 to 3 to form a precipitate which contains a water-soluble vitamin K derivative to be accumulated in the cells and to be released out of the cells. By subjecting this precipitate to separation as by centrifugal separation, a water-soluble vitamin K derivative can be obtained.

Alternatively, *Bacillus subtilis* cells are cultured by a conventional method or the method as described above to obtain a culture medium. The resultant culture medium is separated as by centrifugal separation to obtain a supernatant. Then, the pH of this supernatant is decreased, preferably to a level in the range of 1 to 3 to form a precipitate which contains a water-soluble vitamin K derivative to be released out of the cells. By subjecting this precipitate to separation as by centrifugal separation, a water-soluble vitamin K derivative can be obtained.

Now, this invention will be described more specifically below with reference to working examples.

The amounts of MK-7, MK-4, and vitamin $K_1$ mentioned in the following examples were measured according to the following methods.

Method for Measuring Amounts of Vitamin K's

First, the method for preparing sample cells of fat-soluble MK-7, MK-4, and vitamin $K_1$ will be described below. 1 g (dry weight) of cultured microorganic cells as a sample are extracted with a Soxhlet extractor (SIBATA SPC 34, WATER BATH SIBATA WB-6C, filter paper ADVANTEC 84 24×100 mm) to obtain a fat-soluble fraction. This fraction is extracted from 100 ml of hexane at 80° C. for 6 hours. The resultant extract is diluted with hexane to a total volume of 100 ml. The extract, 100 µl in volume, is intimately mixed with 1.0 ml of distilled water and 1.5 ml of isopropanol and further mixed with 4.9 ml of hexane by using a touch mixer for about 10 seconds. The resultant mixture is centrifuged (3,000 rpm×10 minutes, 20° C.). A 4.0 ml portion of the supernatant (organic layer: aqueous layer=5.8:1.7) is concentrated and dried to hardness by evaporation and the residue is dissolved in 100 µl of ethanol. As a result, an HPLC sample for measuring the amounts of fat-soluble MK-7, MK-4, and vitamin $K_1$ accumulated in the cells (hereinafter referred to as "Soxhlet-HPLC sample") is prepared. The method for measuring the amount of MK-7 by the following HPLC using this Soxhlet-HPLC sample will be referred to as "Soxhlet-HPLC method".

Then, the method for preparing a sample of the water-soluble vitamin K derivative (inclusive of MK-7) will be described herein below. A cultured product is thoroughly kneaded by means of a spatula. To 5 g of the kneaded cells, 45 ml of distilled water is added. The resultant mixture is centrifuged at 3,000 rpm at 20° C. for 10 minutes. The supernatant, 0.5 ml in volume, is used as an extraction sample. To this extraction sample, 0.5 ml of distilled water and 1.5 ml of isopropanol are added and intimately mixed, and then 5.0 ml of hexane is further added. The resultant mixture is stirred and then centrifuged at 3, 000 rpm at 20° C. for 10 minutes. The resultant supernatant, 4.0 ml in volume, is concentrated and dried to hardness by the use of an evaporator and the residue is dissolved in 100 µl of ethanol. Thus, an HPLC sample for measuring the amount of water-soluble MK-7 derivative accumulated in the cells (hereinafter referred to as "HPLC sample",) is prepared. The method for measuring the amount of MK-7 by the following HPLC using this HPLC sample will be referred to as "HPLC method".

As these HPLC samples for measuring the amounts of MK-7, MK-4, and vitamin $K_1$, the relevant cultured broth is used in its unmodified form.

The measurement of the amounts of MK-7, MK-4, and vitamin $K_1$ by the high-performance liquid chromatography (HPLC) makes use of the phenomenon that vitamin K is reduced by a platinum-alumina catalyst into a hydroquinone compound and made to form a fluorescent substance. To be more specific, this measurement is carried out under the following conditions.

| <Apparatus> | |
|---|---|
| Pump: | PU-980 (made by Nippon Bunko K.K.) |
| Injector: | 7125 (made by Nippon Bunko K.K.) |
| Column Oven: | CO-960 (made by Nippon Bunko K.K.) |
| Detector: | Fluorescent Detector 821-FP (made by Nippon Bunko K.K.) |
| Data Processing Device | C-R5A (made by Shimadzu Seisakusho Ltd.) |
| <Conditions> | |
| Column: | ODS-II column (4.6 × 250 mm) (made by Shimadzu Seisakusho Ltd.) |
| Reduction Column: | Platinum-Alumina Catalyst Column (measuring 4.0 mm in diameter and 10 mm in length, made by Wako Pure Chemical Industries Ltd., packed with about 0.2 g of platinum-alumina catalyst of first grade having a Pt content of 5%) |
| Mobile Phase: | 97% ethanol (flow rate: 0.7 ml/min.) |
| Separation·Reduction· Temperature | 40° C. |
| Measuring Wavelength: | Excitation 320 nm and fluorescence 430 nm |
| Amount Injected: | 10 µl |

When calibration curves for MK-7, MK-4, and vitamin $K_1$ were prepared in accordance with the method of measurement described above, the amount of MK-7 could be measured in the range of 0.05 to 50 ng by the formula $[-0.89661+1.6993\times10^{-6}\times(\text{area of the HPLC corresponding to vitamin K } (\mu V, \text{sec}))]$ and the amounts of MK-4 and vitamin $K_1$ could be measured in the range of 0.01 to 10 ng respectively by the formula $[-0.58657+4.8030\times10^{-9}\times(\text{area of the HPLC corresponding to vitamin K } (\mu V, \text{sec}))]$ and the formula $[-0.44381+4.0626\times10^{-7}\times(\text{area of the HPLC corresponding to vitamin K } (\mu V, \text{sec}))]$.

The standard specimen of MK-7 used in the formation of the calibration curves was prepared as follows. Specifically, 600 g of fermented soybeans (natto) and 1 liter of 75% isopropanol and 1 liter of n-hexane added thereto were slowly stirred for one hour and the produced mixture was left standing. The upper layer of the two separated layers was removed, dried with anhydrous sodium sulfate, and evaporated to hardness to obtain about 20 g of an extract. This extract was mixed with 10 ml of n-hexane. The solution was passed for adsorption through 400 ml of a bed of chromatography grade silica gel. The adsorbate was eluted and fractionated with 2 liters of n-hexane/toluene (1:1) mixture. The fractions containing MK-7 were evaporated to dryness under a reduced pressure. The combined silica gel concentrate was dissolved in 5 ml of n-hexane. The resultant solution was fractionated with the silica gel column in the same manner as described above and the fraction was evaporated to dryness under a reduced pressure to obtain a residue, about 350 mg in weight. A 50 mg portion of the residue was dissolved in a small amount of acetone. The resultant solution was passed through a 60 ml column of chromatography grade ODS-silica gel packed with acetonitrile/methanol (1:1) and developed therein with acetonitrile/methanol (1:1). Wile the eluate was monitored by the HPLC, the fraction having eluted solely therein a substance suspected to be MK-7 was separated and dried to hardness under a reduced pressure. The infrared absorption spectrum and the mass spectrum obtained of this substance identified this substance to be MK-7. This substance was tested for purity, to find to have a purity of 99.8%. The standard specimens of phylloquinone (vitamin $K_1$) and menaquinone-4 (MK-4) used herein were relevant reagent grade products of Sigma Corp. The results of the measurement were obtained by averaging the analyses of three extractions.

EXAMPLE 1

10 culture media, each 200 ml in volume, (total amount of 2 liters) was prepared by dissolving dry bouillon (made by Nissui Seiyaku K.K.) in a concentration of 3% in 0.3% malt soup stock in 5 Erlenmeyer flasks having an inner volume of 500 ml, and then sterilized in an autoclave at 130° C. for about 30 minutes. After the sterilized solution was cooled, about $5\times10^8$ cells of Miyagino strain (made by Miyagino Natto Manufactory K.K. in Sendai) was placed in this solution and then shaking-cultured (100 rpm) at 40° C. for 36 hours. The cultured cells were collected, washed, mixed with a substantially equal amount of corn starch, and air dried at 4° C. over a period of three days. The dried mixture consequently obtained contained a large amount of live cells of *Bacillus subtilis* natto (spores and vegetative cells). When it was tested for amount of menaquinone-7 (MK-7) accumulated therein by the HPLC method, it was found to have a menaquinone-7 content of about 331.7 µg per g of dry cells.

Then, five healthy adults were each caused to ingest 1 g of the dry cells at 10 o'clock every morning. After the elapse of a prescribed interval, blood was collected from each of the healthy adults and was tested for MK-7 level in the plasma. The time-course changes of MK-7 level in the plasma were investigated. The results are shown in FIG. 1. It is noted from FIG. 1 that clear acceleration of the level in plasma was recognized and this acceleration was found to last for not less than 24 hours (p<0.05).

EXAMPLE 2

Five healthy adults were each caused to ingest 1 g of dry cells (containing $1.8 \times 10^{10}$ live cells) of Nitto strain (made by Nitto Yakuhin Kogyo K.K. in Kyoto) at 10 o'clock every morning. Then, blood was collected from the adults along the course of time. The plasma was separated from the collected blood and tested for MK-7 level in the plasma in the same manner as in Example 1. The results are shown in Table 1 and FIG. 2. The *Bacillus subtilis* natto used in the present example had a MK-7 content, as determined by the HPLC method, of about 51.0 µg/g of dry cells.

As a control, five healthy adults were caused to ingest purified MK-7 in place of the dry cells of *Bacillus subtilis* natto mentioned above. The plasma similarly obtained from each of the healthy adults was tested for MK-7 level in the plasma. The results are shown in Table 1 below.

and the amounts of MK-7 in the cultured broth and in the cells were measured at prescribed periods.

Figure 3:
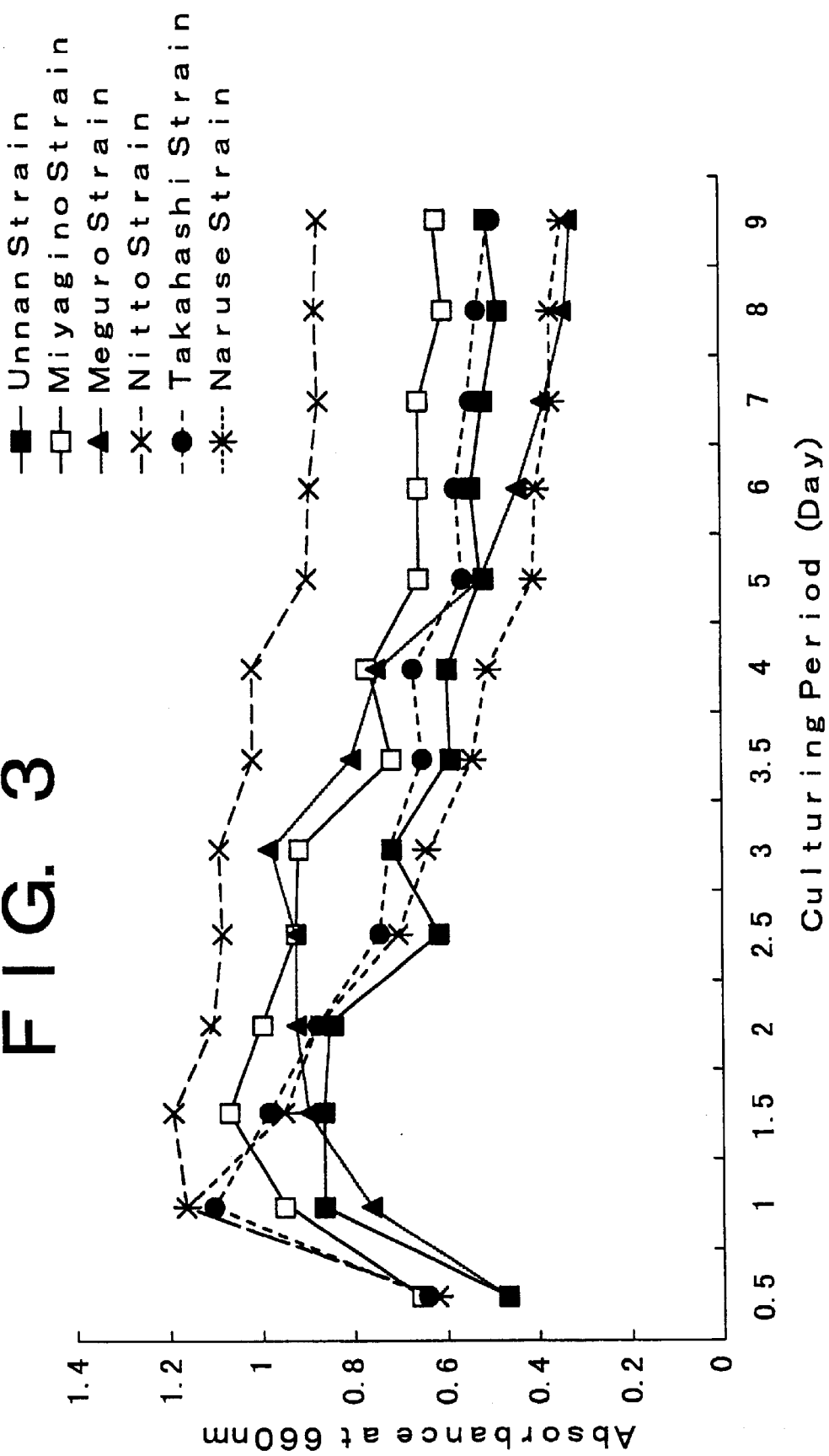
FIG. 3 is a graph showing the growth of various species of *Bacillus subtilis* natto relative to the time of culture in Example 3.
Figure 4:
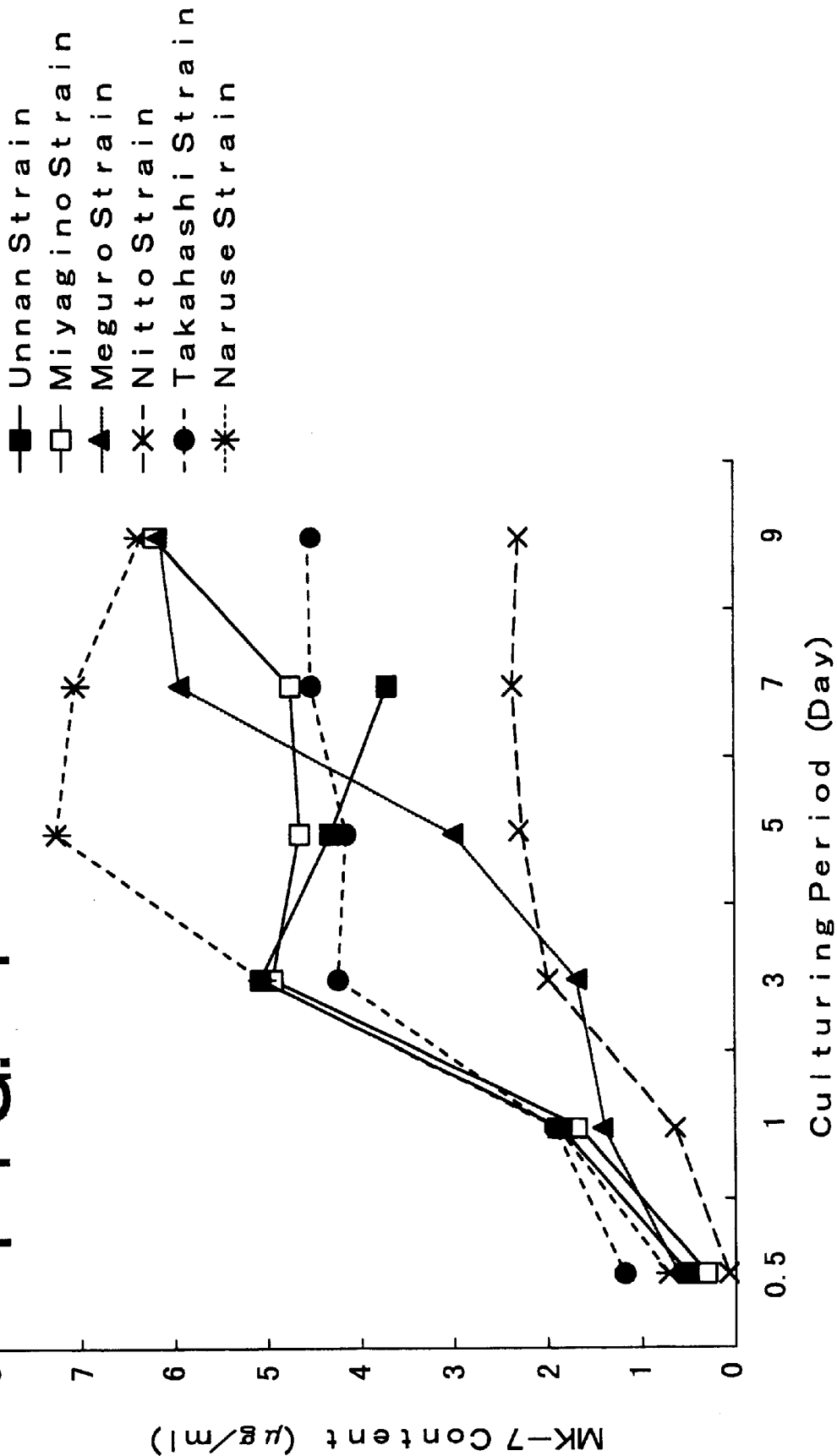
FIG. 4 is a graph showing the amounts of MK-7 in the cultured broths of various species of *Bacillus subtilis* natto relative to the time of culture in Example 3.
Figure 5:
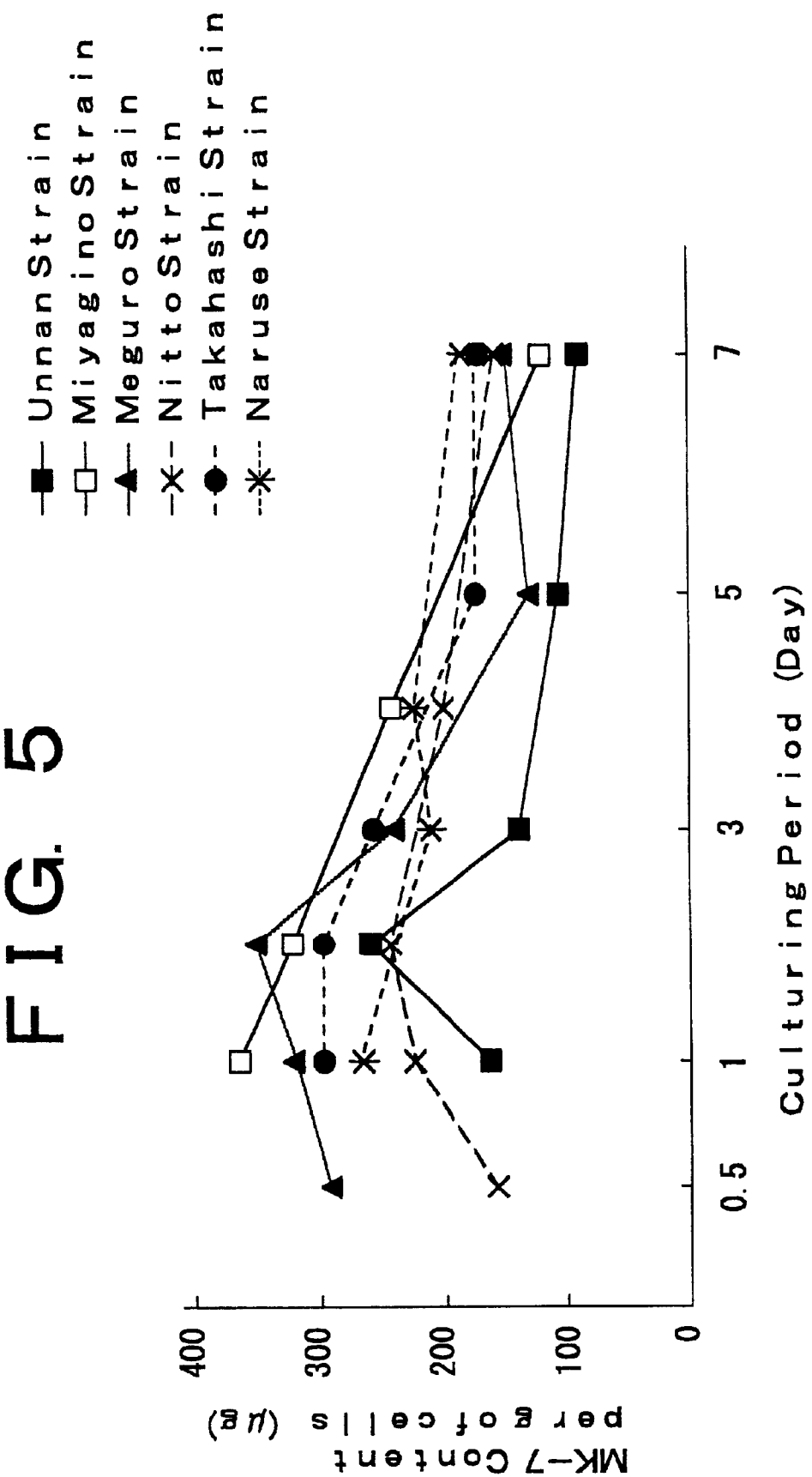
FIG. 5 is a graph showing the amounts of MK-7 accumulated in the cells of various species of *Bacillus subtilis* natto relative to the time of culture in Example 3.

The growth of each species of *Bacillus subtilis* natto, the amount of MK-7 in the cultured broth (µg/ml), and the amount of MK-7 per gram of the cells of each species of *Bacillus subtilis* natto (µg/g) respectively relative to the culturing time are shown in FIG. 3, FIG. 4, and FIG. 5, respectively.

*Bacillus subtilis* Natto Used

- Unnan SL-001 Strain (otherwise called simply as "Unnan")
- Miyagino strain (made by Miyagino Natto Manufactory K.K. in Sendai)
- Meguro strain (made by Meguro Laboratory K.K. in Osaka)
- Nitto strain (made by Nitto Yakuhin Kogyo K.K. in Kyoto)
- Takahashi strain (made by Yuzo Takahashi Laboratory in Sendai)
- Naruse strain (made by Naruse Fermentation Chemical Laboratory K.K. in Tokyo)

Hereinafter, the aforementioned *Bacillus subtilis* natto will be referred to by names of species.

TABLE 1

| | Concentration of MK-7 in plasma (after the elapse of) | | | | | | |
|---|---|---|---|---|---|---|---|
| | 0 hour | 4 hours | 8 hours | 12 hours | 24 hours | 32 hours | 48 hours |
| *B. subtilis* natto (about $1.8 \times 10^{10}$ cells/g) | 1.2 ± 1.1 | 7.5 ± 2.7** | 5.0 ± 1.0** | 4.8 ± 13** | 4.3 ± 1.9* | 4.8 ± 0.9** | 3.1 ± 0.6* |
| Purified 14K-7 (about 51.0 µg) | 1.3 ± 1.1 | 11.2 ± 2.8** | 7.3 ± 1.6** | 4.3 ± 1.0** | 2.2 ± 1.0 | 1.4 ± 0.72† | 1.4 ± 0.9† |

In the table, the numerical values represent the MK-7 levels (average ± standard deviation) in plasma of relevant groups of collection.
Significant differences relative to the numerical values before ingestion: *p < 0.05, ** p < 0.005; and
†Significant difference between the two groups after 32 and 48 hours: p < 0.005 (n = 5).

Figure 2:
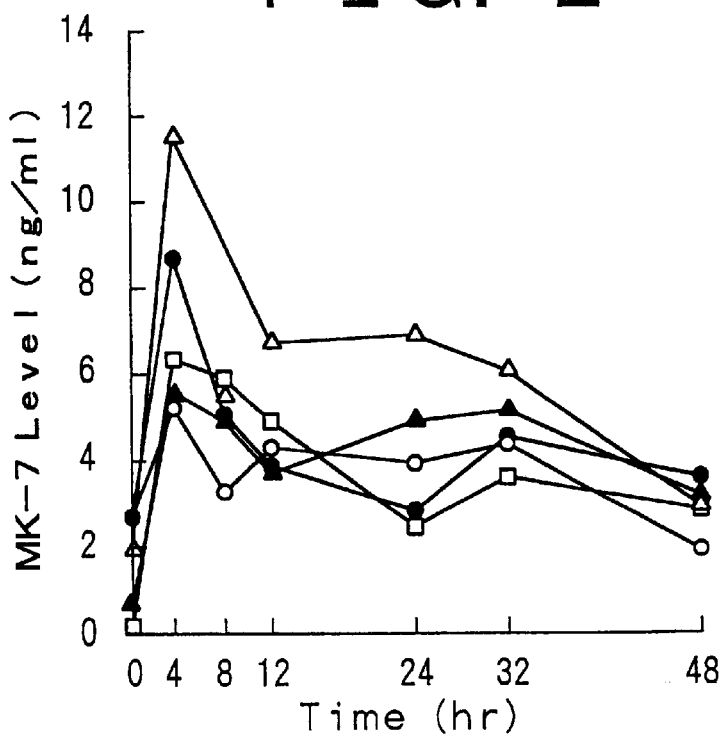
FIG. 2 is a graph showing time-course changes in levels of vitamin K (manequinone-7) in plasma of five healthy adults each having orally ingested a dose of $1.8 \times 10^{10}$ cells of dry *Bacillus subtilis* natto prepared in Example 2.

It is noted from the results shown in Table 1 and FIG. 2 that a significant acceleration of the MK-7 level in plasma reaching the peak on the fourth hour after the ingestion was recognized (p<0.005) invariably in both the groups, that the effect of accelerating the Level in plasma lasted for a far longer time in the group of adults having ingested *Bacillus subtilis* natto, and that particularly the effect in and after the 32nd hour had a significant difference between that of the group of adults having ingested MK-7 and that of the group of adults having pure MK-7.

With this amount of ingestion, none of the groups was recognized to brig any significant change in the activity of the blood coagulation-fibrinolysis system as investigated by the thromboelastography, the activated partial thromboplastin time, the plasma prothrombin, or the protein C content. Incidentally, the thromboelastography (TEG) pattern of the blood was investigated with the device made by Hellige Corp. and the prothrombin time (PT) and the activated thromboplastic time (APTT) were determined with the instrument made by Erma Corp. and sold under trademark designation of Clot Digitim TE20 apparatus.

EXAMPLE 3

The following six species of *Bacillus subtilis* natto were each shaking-cultured (100 rpm) at 30° C. in 300 ml of a culture medium containing 3% nutrient broth (dry bouillon) (made by Nippon Seiyaku K.K.) and held in an Erlenmeyer flask, 500 ml in inner volume. The growth of the microorganic cells was determined in terms of absorbance at 660 nm It is noted from FIG. 3 that the microorganic growth showed a similar behavior in all the species of *Bacillus subtilis* natto and the growth expressed in terms of average absorbance at 660 nm (n=6) was 0.583 on the 0.5th day, 1.011 on the first day, 0.948 on the second day, 0.854 on the third day, 0.592 on the fifth day, and 0.552 on the seventh day, and that the microorganic growth reached the stationary state on the first—second day after start of the culture. As respects the amount of MK-7 released into the culture broth, it is noted from FIG. 4 that all the species of *Bacillus subtilis* natto manifested a similar behavior and the average amount for the six species of *Bacillus subtilis* natto was 0.563 µg/ml on the 0.5th day, 1.592 µg/ml on the first day, 3.867 µg/ml on the third day, 4.317 µg/ml on the fifth day, and 4.784 µg/ml on the seventh day. These facts indicate that the amount of MK-7 released into the culture medium abruptly increased rather on and after the second day than on the first—second day on which the microorganic growth reached the stationary state and that the MK-7 was released in a large amount into the culture medium particularly on and after the fourth day. The amount of MK-7 reduced to the amount of MK-7 per g of the microorganic cells (similarly all the species of *Bacillus subtilis* natto exhibited a similar behavior), as shown in FIG. 5, reached the maximum (about 300 µg/g of dry cells on the average) on the second day and rather began to decrease on and after the fourth day on which the release in a large amount into the culture medium started, as though proportionally to the results mentioned above.

EXAMPLE 4

Bean-curd refuse (made by Asahimatsu Shokuhin K.K. in Iida-shi) was stored in a frozen state at −25° C. and, when necessary, defrosted and put to use. The defrosted bean curd refuse was sterilized in an autoclave at 120° C. for 30 minutes and placed in a container of polystyrene paper (PSP) having an inner volume of about 120 ml and used as a culture medium for Bacillus subtilis natto.

A total of seven species of Bacillus subtilis natto, i.e. four strains of Bacillus subtilis natto (Takahashi strain, Naruse strain, Miyagino strain, and Asahi strain) used in commercially available fermented soybeans, two strains of Bacillus subtilis natto (Nitto strain and Merugo) used in medicines, and a strain of Bacillus subtilis natto separated from the fermented soybeans from Unnan Province of China (Unnan SL-001 strain), were each shaking-cultured (100 rpm) at 37° C. for three days in 150 ml of a culture medium containing 3% nutrient broth (made by Nippon Seiyaku K.K.) and held in an Erlenmeyer flask, 500 ml in inner volume to prepare pre-cultured broths of the seven species of Bacillus subtilis natto mentioned above. 0.5 ml of the pre-cultured broths of the total of seven species of Bacillus subtilis natto (live cell number: $2>10^8$ cells/ml) were each added to the bean-curd refuse prepared as described above (50 g of wet weight) and left standing at 37° C. for eight days to undergo continued fermentation.

Figure 6:
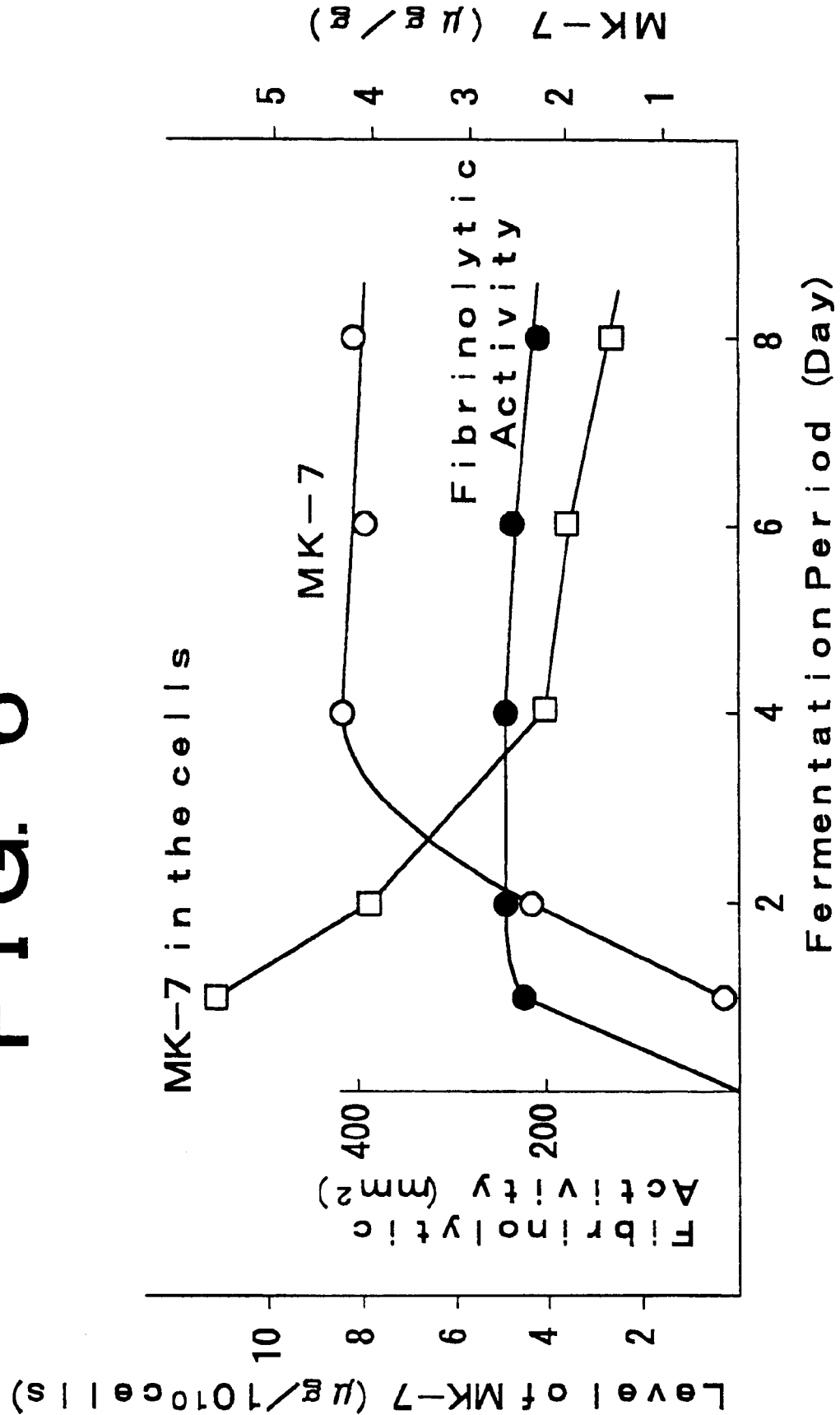
FIG. 6 is a graph showing the amounts of MK-7 accumulated in the cells, the fibrinolytic activity, and the amount of MK-7 released from the cells in Example 4.

After the elapse of prescribed numbers of days (1, 2, 4, 6, and 8 days) after start of the fermentation, the Bacillus subtilis natto was suspended in water and the suspension was filtered through a tea strainer made of metal and then centrifuged (3,000 rpm×10 minutes) to prepare relevant cultured microorganic cells. These cultured cells were used as Soxhlet-HPLC samples for the measurement of MK-7. The Soxhlet-HPLC samples thus prepared were tested for the amount of MK-7 and the fibrinolytic activity (thrombolysis). The results are shown in FIG. 6.

It is noted from FIG. 6 that the level of MK-7 in the microorganic cells per $10^{10}$ cells increased on the first—second day and decreased thereafter, that the release of MK-7 into the culture medium proceeded proportionately to the behavior of the concentration, and that the amount of MK-7 released into the culture medium reached the peak on the fourth day which was later than the time at which the thrombolytic activity by nattokinase (NK) reaching the peak on the second day after start of the fermentation began to increase (the activity reaching the maximum within two days of starting the fermentation by the standard fibrin plate method and the synthetic substrate decomposition method alike).

In all the species of Bacillus subtilis natto, such high levels of MK-7 productivity as exceed 1.9 μg per g of the wet weight of bean curd refuse were recognized (the average amount of MK-7 dissolved in water was 36.6 μg/g of the wet weight of bean curd refuse in Unnan; 1.9 μg/g of the wet weight of bean curd refuse in Miyagino strain; 14.2 μg/g of the wet weight of bean curd refuse in Naruse strain; 6.8 μg/g of the wet weight of bean curd refuse in Takahashi strain; 11.9 μg/g of the weight of bean curd refuse in Asahi strain; 1.9 μg/g of the wet weight of bean curd refuse in Meguro strain; and 5.2 μg/g of the weight of bean curd refuse in Nitto strain). Particularly, Unnan showed such a high level of MK-7 productivity as 36.6 μg/g of the wet weight of bean curd refuse. This value is shown by calculation to be so high as 2 to 20 times the level of productivity obtained by other species of Bacillus subtilis natto and so high as not less than four times the levels of analyses of fermented soybeans (6.2 to 8.7 μg/g of the wet weight of bean curd refuse) reported heretofore [Table of Japanese Food Product Components, complied by Michio Yamaguchi, published by Ishiyaku Shuppan, Tokyo, 1997, pp. 52–53; Toshiyuki Sakano et al., Vitamins, 62, 393–398 (1988); H. Ikeda and Y. Doi, Eur. J. Biochem., 192, 219–223 (1990); and H. Ikeda, Kaseishi, 43, 643–648 (1992)].

EXAMPLE 5

Nitto strain was added in such an amount to 300 ml of a liquid culture medium containing 0.5, 2, or 3% of polypeptone S (made by Wako Pure Chemical Industries Ltd.) and held in an Erlenmeyer flask, 500 ml in inner volume that the culture medium contained $2\times10^5$ live microorganic cells per ml and shaking-cultured (100 rpm) therein at 37° C. for two days. The resultant culture broth was centrifuged (3,000 rpm×10 minutes) to separate a supernatant and microorganic cells. The cells were washed with water and freeze dried.

The amount of MK-7 in the culture supernatant thus prepared was measured by the HPLC method and the amount of MK-7 in the microorganic cells was measured by the Soxhlet-HPLC method. The results are shown in Table 2 below. The yield of microorganic cells in the culture media having polypeptone S concentrations of 0.5 and 3% were respectively 0.24 g (weight of dry cells) and 1.18 g (weight of dry cells) per 600 ml of culture medium (for two flasks).

TABLE 2

| Polypeptone S Concentration | Amount of MK-7 in supernatant (μg/ml) | Amount of MK-7 in microorganic cells (μg/g of dry cells) |
| --- | --- | --- |
| 0.5% | 1.11 | 73.4 |
| 2% | 0.62 | 140.0 |
| 3% | 0.51 | 245.3 |

EXAMPLE 6

Meguro strain was shaking-cultured at 41° C. for two days. The culture broth consequently obtained was centrifuged to separate a supernatant and microorganic cells.

Then, an aliquot, 1.011 g (dry weight), of the microorganic cells (number of cells: $5\times10^{11}$) thus prepared was adopted as a sample and extracted by the use of a Soxhlet extractor (SIBATA SPC 34, WATER BATH SIBATA WB-6C, filter paper ADVANTEC 84 24×100 mm) to obtain a fat-soluble fraction over a period of 6 hours. This fraction was extracted from 100 ml of hexane at 80° C. for 6 hours. The liquid extract was diluted with hexane to a total volume of 100 ml. The extract, 100 μl in volume, was intimately mixed with 1.0 ml of distilled water and 1.5 ml of isopropanol and further mixed with 4.9 ml of hexane by the use of a touch mixer for about 10 seconds. The resultant mixture was centrifuged (3,000 rpm×10 minutes, 20° C.). The produced supernatant (organic layer:water layer=5.8:1.7), 14 ml in volume, was dried to hardness and the dry residue was dissolved in 100 μl of ethanol. When the sample thus obtained was tested for the MK-7 content by the Soxhlet-HPLC method, the content was found to be 672.6 μg/g of dry cells.

EXAMPLE 7

Meguro strain was cultured at 37° C. for two days which period can make the largest amount of a vitamin K derivative accumulated within the cells. The cultured product thus obtained was washed with distilled water and then freeze-dried. Five healthy adults (A to E) were each caused to ingest an enteric capsule in which 1 g of freeze-dried product (containing $5\times10^{11}$ cells/g of dried product) was filled. In this case, the MK-7 content was determined by the Soxhlet- HPLC method method, to find to be 708.0 μg/g of dried product. At prescribed points, blood was collected from the adults along the course of time. The plasma MK-7 level was tested in the same manner as in Example 1. The results are shown in Table 3.

TABLE 3

| Healthy Adult | Plasma MK-7 Level at Prescribed Points after Administration of Enteric Capsule (ng/ml) | | | | |
|---|---|---|---|---|---|
| | 0 Day | 0.5 Day | 1 Day | 3 Days | 7 Days |
| A | 1.1 | 9.3 | 8.9 | 4.5 | 2.4 |
| B | 1.0 | 10.6 | 7.4 | 5.1 | 2.2 |
| C | 0.9 | 9.1 | 8.2 | 2.6 | 1.9 |
| D | 0.6 | 6.8 | 6.9 | 2.3 | 1.4 |
| E | 0.8 | 8.7 | 6.6 | 2.6 | 1.7 |
| Average | 0.88 ± 0.19 | 8.90 ± 1.37* | 7.60 ± 0.95* | 3.42 ± 1.28* | 1.92 ± 0.40* |

*$p < 0.005$

The results shown in Table 3 indicates a significant acceleration of the MK-7 level in plasma. At the same time, as shown in Table 3, the MK-7 level in plasma was kept at a level of about 2 times as high as the normal plasma MK-7 level (0.88±0.19 ng/ml) for at least one week and thus this acceleration continues over an extremely long period.

EXAMPLE 8

Figure 7:
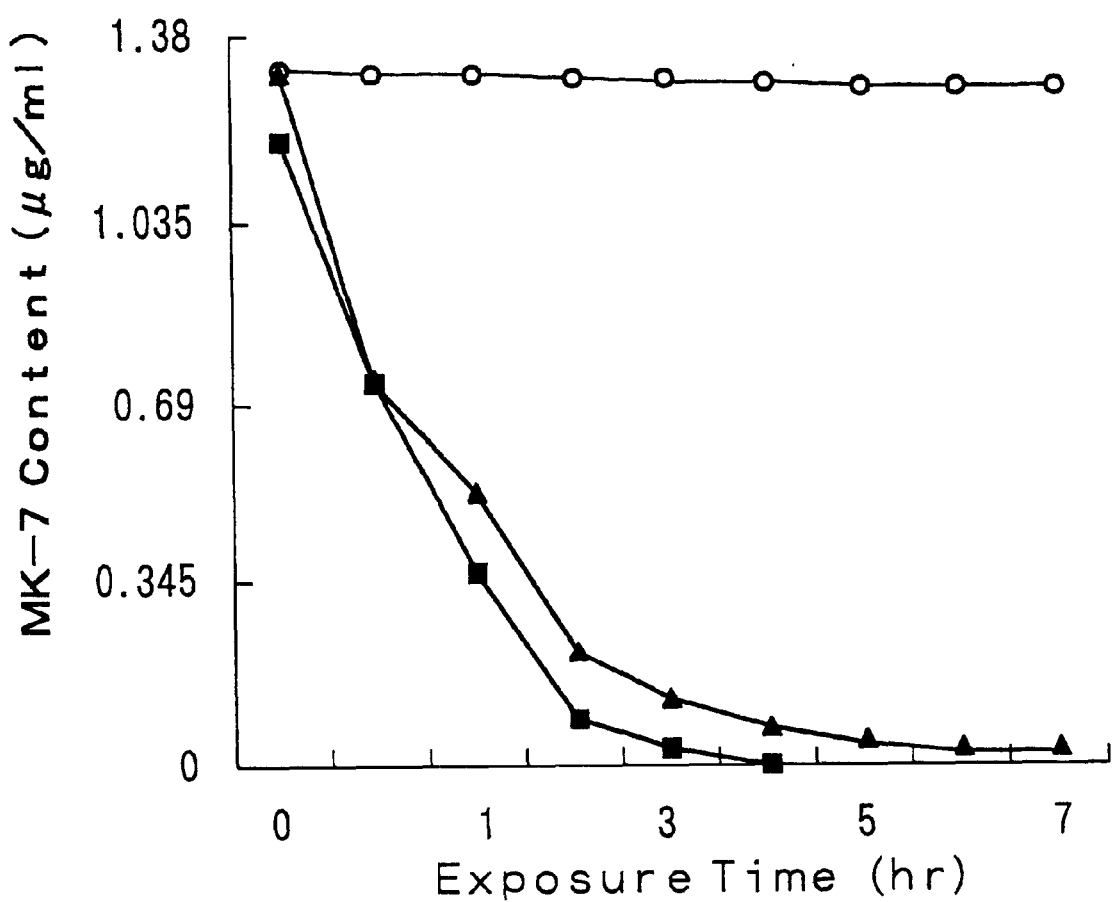
FIG. 7 is a graph showing the amounts of MK-7 relative to the time of exposure to the light of a fluorescent lamp in Example 7 and Comparative Example 1.

The MK-7 prepared from Meguro strain in the same manner as in Example 6 was dried to obtain drain MK-7 in the form of white powder. This dry MK-7 was exposed to the light from a fluorescent lamp at room temperature for 5 hours. In this case, the amount of MK-7 was measured along the course of time in the same manner as in Example 6. The results are shown in FIG. 7 (indicated by empty circle (○) marks). The amount of MK-7 showed virtually no change on exposure to the light from the fluorescent lamp as noted from FIG. 7, indicating that the MK-7 obtained by the method of the present invention manifests significantly excellent stability to withstand the light (photostability).

When the dry MK-7 prepared as described above was exposed continuously to the light of the fluorescent lamp for one week under the same conditions as mentioned above and then tested for the MK-7 content, virtually no change was recognized.

Comparative Example 1

Microorganic cells were prepared in the same manner as in Example 6. In a mortar, 2 g of the cells were placed and 3 g of sea sand and 3 ml of water were added to the cells in the mortar. Then, the content of the mortar was stirred and extracted with acetone (20 ml×4) and suction filtered by the use of a glass filter. The filtrate was wholly transferred into a separation funnel and extracted from 100 ml of diethyl ether and 50 ml of water to separate an ether layer. The aqueous layer was combined with 100 ml of diethyl ether for further separation of the ether layer. The ether layers thus separated were combined, distilled to expel the solvent by evaporation, and subjected to silica gel chromatography (hexane 10 ml and silica gel 5 g). The adsorbate on the silica gel was eluted with 30 ml of hexane/diethyl ether [85/15 (v/v)]. The eluate was further distilled to expel the solvent by evaporation. The residue was dissolved in 2-propanol to prepare a fat-soluble MK-7.

The fat-soluble MK-7 thus prepared was dried to obtain a dry product of MK-7. This dry product of MK-7 was irradiated with the light from a fluorescent lamp at room temperature for 5 hours and then tested for the fat-soluble M-7 content in the same manner as in Example 6. The results are shown in FIG. 7 (indicated by filled square (■) marks). The amount of MK-7 could not be measured after the sample was exposed to the light from the fluorescent lamp for about 3 hours as noted from FIG. 7, indicating that the MK-7 thus prepared lacks in photostability.

EXAMPLE 9

Nitto strain was shaking-cultured and the resultant culture broth was centrifuged to separate a supernatant and microorganic cells. When the amount of MK-7 in the cultured microorganic cells thus prepared was measured by the Soxhlet-HPLC method, the content was found to be 564.0 μg/g of dry cells, in terms of MK-7 amount.

0.1 g of aliquot of the cells and 5 ml of distilled water added-thereto were subjected to sonication. Then, the sonicated liquid was centrifuged. When the amount of the water-soluble MK-7 derivative in the supernatant was measured by the HPLC method, the content was found to be 52.6 μg/g of dry cells.

Figure 8:
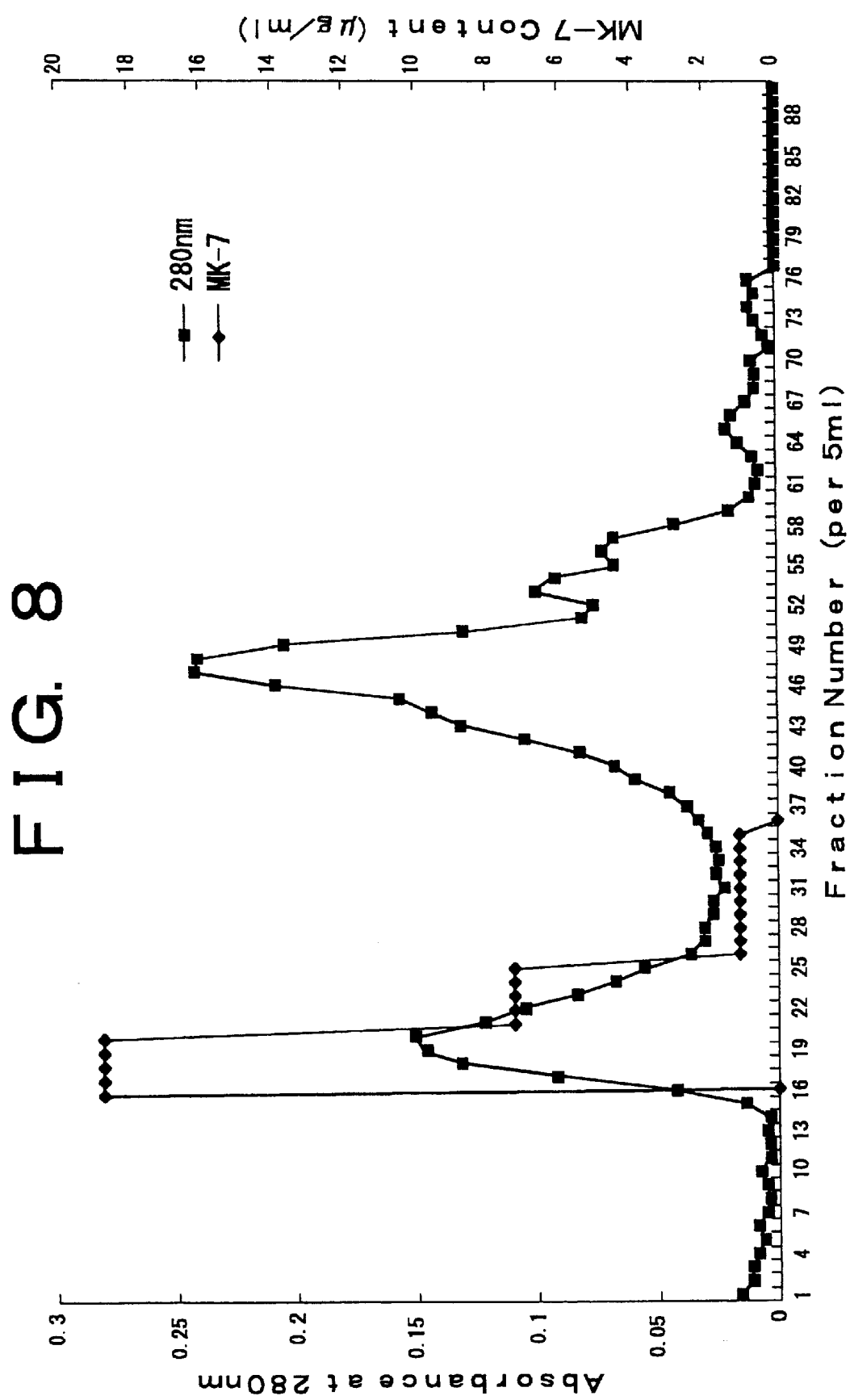
FIG. 8 is a graph showing the patterns during gel filtration and the amount of MK-7 in each fraction in Example 10.

Then, a solution of the water-soluble MK-7 derivative in water was subjected to gel filtration by the use of a Sephadex G50 column (2.5×50 cm: equilibrated in advance with a 0.05M phosphate buffer containing 0.15M NaCl, pH 7.5). The content of MK-7 in each fraction was measured by the HPLC method. The results are shown in FIG. 8. It is noted from FIG. 8 that the portions containing MK-7 in large amounts (Fraction Nos. 17 to 25) were eluted in fairly higher molecular weight regions than the amino acid portions (Fraction Nos. 46 to 49).

EXAMPLE 10

The bean curd refuse offered by Asahimatsu Shokuhin K.K. in Iida-shi was stored in a frozen state at −25° C. and, when necessary, defrosted and put to use.

Separately, a pre-cultured broth of *Bacillus subtilis* natto was prepared by shaking-culturing (100 rpm) a strain of *Bacillus subtilis* natto separated from fermented soybeans imported from Unnan Province of China (Unnan SL-110 Strain) at 37° C. for 3 days in 150 ml of a culture medium containing 3% nutrient broth (dry bouillon) (made by Nissui Seiyaku K.K.) in an Erlenmeyer flask having an inner volume of 500 ml.

The defrosted bean curd refuse, 1 kg in wet weight, was sterilized in an autoclave at 120° C. for 30 minutes and then placed in a container of polystyrene paper (PSP). In this container, the pre-cultured broth of *Bacillus subtilis* natto prepared as described above was placed and left fermenting at 37° C. for 4 days. The bean curd refuse, 1 kg in wet weight which had been fermented as described above and 5 liters of water added thereto were stirred at room temperature for one hour and centrifuged (3,000 rpm×10 minutes). The supernatant and 620 g of an ion-exchange resin (DEAE-Sepharose CL-613) added thereto were stirred and then left standing at room temperature for 30 minutes. Then, the resultant mixture was filled in a glass column (7.5 cm in diameter×100 cm), washed with distilled water and 0. 05 M phosphate buffer (pH 7.0), and subjected to gradient elution with 0.05 M phosphate buffer (pH 7.0) containing 0.1 to 0.8 M NaCl. The amounts of vitamin K were measured by the HPLC. The fraction containing vitamin K was concentrated by the use of a membrane filter (molecular weight 10,000, made by Millipore Corp.), dialyzed against distilled water, and then freeze-dried to obtain a water-soluble vitamin K derivative in the form of a light yellow powder.

Figure 9:
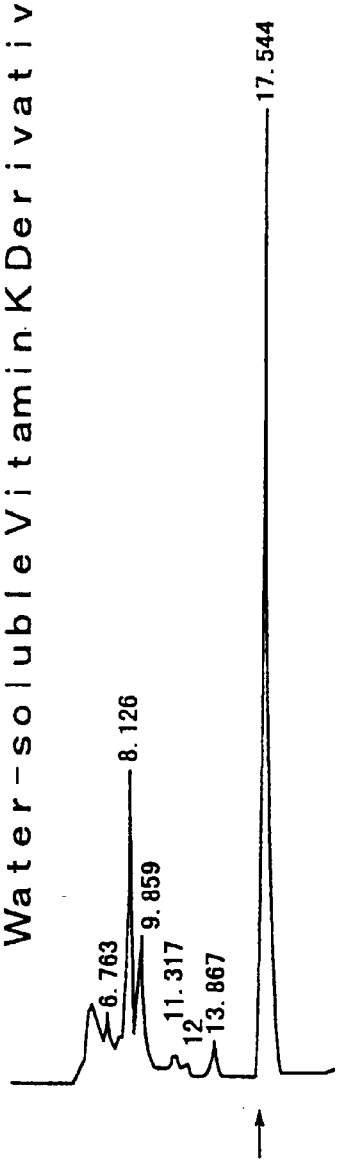
FIG. 9 is a graph showing the results of the HPLC analysis performed on a water-soluble vitamin K derivative and an isopropanol extract of tofu (bean curd) refuse in Example 9.
Figure 9:
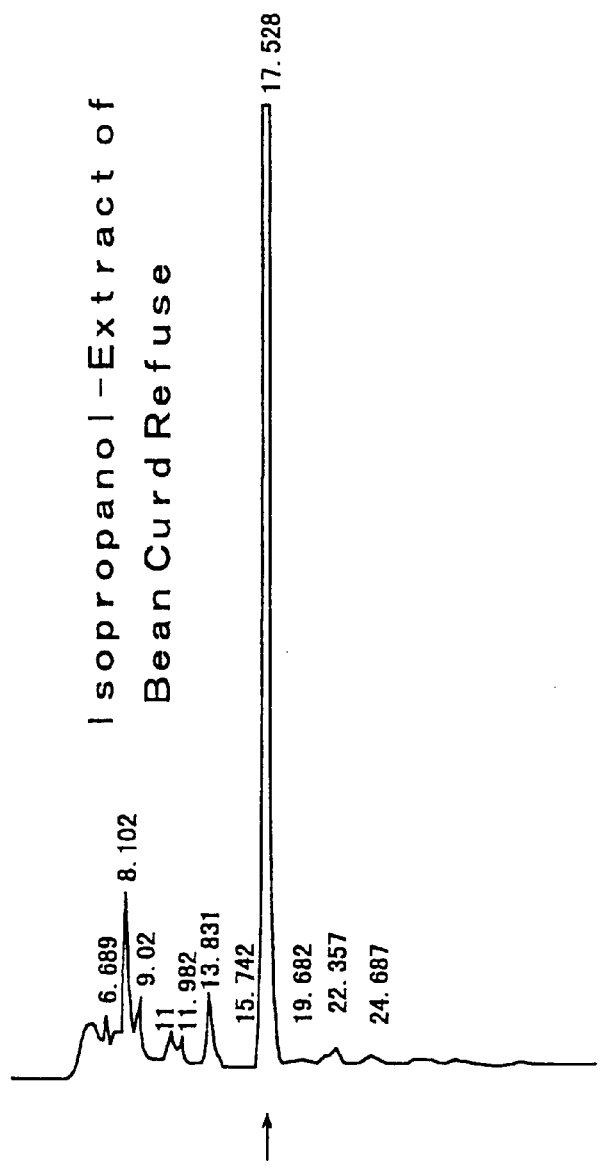

The water-soluble vitamin K derivative obtained as described above and the extract of the same bean cure refuse as mentioned above from isopropanol were analyzed by the HPLC. The results are shown in FIG. 9. In FIG. 9, the intervals of retention of MK-4, vitamin $K_1$, and MK7 were respectively about 8.2 minutes, about 11.3 minutes, and about 17.5 minutes. The arrow mark indicates the retention time of MK-7. It is noted from FIG. 9 that a portion of not less than 60% of the extract of bean curd refuse from isopropanol was extracted in the water-soluble fraction, that the amounts of vitamin $K_1$ and MK-4 were small as vitamin K, and that a portion of not less than 95% was always occupied by MK-7.

When the water-soluble vitamin K derivative was analyzed by the SDS-polyacrylamide gel electrophoresis, it showed a sole band, though large in width, at the position of a molecular weight of about 100,000. From the results, it is inferred that the water-soluble vitamin K derivative forms a complex of a molecular weight of about 100,000 with other glycoprotein. The yield of water-soluble vitamin K derivative from 1 kg of fermented soybeans was about 5.3 g (inclusive of 830 µg of water-soluble MK-7 derivative/g), an average of the results of three procedures.

EXAMPLE 11

5 Erlenmeyer flasks (an inner volume of 500 ml) each having 300 ml of 3% dry bouillon (made by Nissui Seiyaku K.K.) media placed therein were sterilized in an autoclave at 120° C. for 15 minutes. In these media, each one loop of Unnan SL-001 strain was inoculated and shaking-cultured (100 rpm) at 37° C. After 4 days, the combined medium was centrifuged (5,000 rpm×10 minutes), and the supernatant was divided into three so as to make each the volume thereof 400 ml. Then, the pH value of each aliquot was adjusted to 1.02, 2.07 and 3.01 with dilute hydrochloric acid. These aliquots were left standing at a room temperature for three hours and then centrifuged (5,000 rpm×10 minutes, at 10° C.), to obtain and separate a white precipitate. Each precipitate was dissolved in a small amount of distilled water, made the pH value adjusted to 7.0 with ammonium bicarbonate, and thereafter freeze-dried. The freeze-dried products were weighed to find to be 0.52 g, 0.28 g and 0.31 g, in the case of the pH of 1.02, 2.07 and 3.01, respectively. Further, these freeze-dried products were tested for the MK-7 contents by the Soxhlet-HPLC method to find that the MK-7 contents in the case of the pH of 1.02, 2.07 and 3.01 were 2,800 µg/g dry product, 2,200 µg/g dry product and 2,000 µg/g dry product, respectively. Furthermore, solutions having 15 mg of each freeze-dried product added to 5 ml of distilled water were centrifuged (10,000 rpm×10 minutes). The supernatants (i.e. water-soluble fractions) were similarly tested for the MK-7 content to find that the MK-7 contents were 1, 500 µg/g dry product, 1,800 µg/g dry product and 1,800 µg/g dry product, in the case of the pH of 1.02, 2.07 and 3.01, respectively, indicating that the solubility of each water-soluble fraction was about 54%, about 82% and about 90%, respectively.

EXAMPLE 12

3.9 kg of Soybean which had been immersed in tap water overnight was sterilized in an autoclave at 105° C. for 30 minutes, and then spread in two stainless trays of 1 m² in size. To these trays, 100 ml of a sterilized water having added in 100 ml of sterilized water 10 loops of Bacillus subtilis Warburgt (Oyo Biseibutsu Kenkyusho of Tokyo University, IAM 12118 strain) which was cultured on a slant of a nutrient agar medium was inoculated. A lid of urethane was placed on each tray and stationary-cultured at 37° C. for 4 days. After 4 days, the combined weight of fermented soybean (of 2 trays) was about 4.5 kg. Then, 10 liters of distilled water was added to this fermented soybean, stirred intimately, and filtered through a metal gauze covered with gauze (mesh of 10 mm). The water-soluble MK-7 content of the resultant filtrate was determined by the HPLC method to find that total amount (i.e., per 4.5 kg fermented soybean (wet weight)) of 29.8 mg/g could be recovered.

EXAMPLE 13

300 ml of a culture medium containing 2% of polypeptone-S (made by Wako Pure Chemical Industries Ltd.) was placed in an Erlenmeyer flask, 500 ml in inner volume and sterilized in an autoclave at 120° C. for 15 minutes. To this medium, one loop of Bacillus subtilis Warburgt (Oyo Biseibutsu Kenkyusho of Tokyo University, IAM 12118 strain) was inoculated and shaking-cultured (100 rpm) therein at 37° C. for 4 days. The cultured medium was centrifuged (6,000 rpm×10 minutes) to separate a supernatant and microorganic cells. The cells were washed with water and freeze dried.

The supernatant was tested by the HPLC method for the MK-7 content to find to be 140 µg/100 ml. Further, the freeze dried cells were tested by the Soxhlet-HPLC method for the MK-7 content to find to be 22 mg/100 g dried cell.

EXAMPLE 14

Five healthy adults (21 to 63 years old, male) requested to abstain from breakfast were each made to ingest 1,000 µg of the water-soluble vitamin K derivative containing the water-soluble MK-7 derivative prepared in Example 9 at 10 o'clock in the morning. Blood was collected from the healthy adults along the course of time after the ingestion and measured for the level of the water-soluble MK-7 derivative in plasma. As a control, the experiment was repeated with the ingestion of 1,000 µg of purified MK-7 instead. The healthy adults who participated in the experiment of this example had no past illness and showed no abnormality in the plasma test.

It is found from the results that the main vitamin in plasma was MK-7, that the level of the water-soluble MK-7 derivative in plasma which was 1.3±0.8 ng/ml (plasma) before the ingestion rose to 49.9±29.1 ng/ml (p<0.05), a value about 40 times the initial value, on the fourth hour after the ingestion, and that the effect of acceleration thereof lasted for far greater lengths of time than that attained by the ingestion of purified MK-7 in the same amount (on the 24th hour, the level was 21.0±12.1 ng/ml, p<0.05, in the group of the water-soluble MK-7 derivative, while the level was 3.2±2.3 ng/ml in the group of purified MK-7).

EXAMPLE 14

In a kettle, 400 g of milk, 80 g of sugar, and 8 g of corn starch were mixed by stirring and meanwhile heated. The mixture was cooled with the fire turned down immediately before the content of the kettle boiled. The mixed liquid thus cooled and 10 g of a freeze dried cultured product of Miyagino strain produced in the same manner as in Example 3 (730 µg of vitamin K/g of dry cells) added thereto were thoroughly stirred for about two minutes. Separately, in a bowl, 40 g of egg yolk was whipped. The whipped egg yolk and the stirred mixture mentioned above added wholly thereto gradually were mixed. Subsequently, the produced mixture was cooled with water and then cooled to below 10° C. in a refrigerator. Finally, the cooled mixture and 150 g of whipped fresh cream and 5 g of vanilla essence added thereto were cooled to hardness in an ice cream freezer to manufacture a vitamin K-containing ice cream.

EXAMPLE 15

In a jar fermenter, 2 liters in inner volume, Nitto strain was inoculated to 0.8 liter of a culture medium (containing 10 g of glucose, 5 g of polypeptone, and 5 g of yeast extract dissolved in 1 liter of water) and fermented at 40° C. for 1.5 days by aeration culture by diffusion (stirring rate of 500 rpm and aeration rate of 0.5 liter/minute).

The amount of MK-7 in the cultured product of Nitto strain obtained as described above was measured by the conventional method (Sakano et al., Vitamins, 62: 393–398, 1988). Briefly, the measurement was carried out by freeze-drying the cultured product of Nitto strain obtained as described above, causing 0.1 g of the freeze-dried powder and 10 ml of isopropanol added thereto to be stirred and extracted in a touch mixer, and then centrifuging the resultant mixture (3,000 rpm×10 minutes). 100 μl of portion of the supernatant was intimately mixed with 1.0 ml of water and 1.5 ml of isopropanol and further mixed with 4.9 ml of hexane for about 20 seconds in a touch mixer. The resultant mixture was centrifuged (3,000 rpm×10 minutes, at 20° C.). A 4.0 ml portion of the supernatant (organic layer:water layer=5.8:1.7) was concentrated and dried to hardness by evaporation and dissolved in 100 μl of ethanol. When the sample thus prepared was measured for the MK-7 content in the cultured product under the same conditions as the HPLC conditions described in the preceding paragraph concerning the method for measuring the amounts of various species of vitamin K, the amount of MK-7 was found to be 15.1 μg/g. When the procedure just described was repeated by using a chloroform/methanol (1:1) mixture and ether respectively in place of isopropanol, the amount of MK-7 was found to be 15.0 μg/g and 13.6 μg/g, respectively. These amounts were nearly equal to the amount of MK-7 obtained when isopropanol was used.

In contrast, the cultured product of Nitto strain obtained in the same manner as described above was measured for the amount of MK-7 by the Soxhlet-HPLC method. As a result, the amount of MK-7 in the cultured product of Nitto strain was found to be 564.0 μg/g.

These results indicate that the Soxhlet-HPLC method according to the present invention improved the efficiency of extraction of MK-7 and measured satisfactorily the MK-7 content in the cultured product, while the conventional method allowed efficient extraction of the microorganic cells of *Bacillus subtilis* natto only with difficulty and failed to measure the MK-7 content in the cultured product satisfactorily.

The entire disclosure of Japanese Patent Application Nos. 10–172,019 and 11–111,364 filed on May 17, 1998 and Apr. 19, 1999 including specification, claims, drawings and summary are incorporated herein by reference in its entirety.

What is claimed is:

1. A method of producing an edible composition of *Bacillus subtilis* natto cells containing a water soluble vitamin $K_2$ which method comprises the steps of culturing *Bacillus subtilis* natto in a culture medium to produce cultured *Bacillus subtilis* natto, collecting the cultured cells from the culture medium before vitamin $K_2$ produced within the cultured cells is released from the cells, and drying the collected cultured cells.

2. A method according to claim 1, wherein said cultured cells are collected from the culture medium at a time during the culturing process when the cultured cells are in the process of shifting from a logarithmic growth phase to a maximum stationary phase.

3. A method according to claim 2, wherein the step of collecting the cultured cells from the culture medium comprises terminating the culturing process.

4. A method according to claim 1, wherein said cultured cells are collected from the culture medium during a time during the culturing process when the cultured cells are in the process of shifting from a logarithmic growth phase to a maximum stationary phase and before nattokinase is produced.

5. A method according to claim 4, wherein the step of collecting the cultured cells from the culture medium comprises terminating the culturing process.

6. A method according to claim 1, wherein the edible composition is incorporated into a beverage.

7. A method according to claim 1, wherein the edible composition is incorporated into a feed.

8. A method according to claim 1, wherein the step of collecting the cultured cells from the culture medium comprises terminating the culturing process.

9. A method according to claim 1, wherein the *Bacillus subtilis* cells that are cultured are from the Unnan SL-011 strain.

10. A method according to claim 1, wherein water soluble vitamin $K_2$ comprises menaquinone-7.

* * * * *

UNITED STATES PATENT AND TRADEMARK OFFICE
CERTIFICATE OF CORRECTION

PATENT NO.    : 6,677,143 B2
DATED         : January 13, 2004
INVENTOR(S)   : Hiroyuki Sumi It is certified that error appears in the above-identified patent and that said Letters Patent is hereby corrected as shown below:

<u>Title page,</u>
Item [73], the Assignee name should be changed from "Honda Trading Company" to -- Honda Trading Corporation --

Signed and Sealed this

Thirteenth Day of April, 2004

JON W. DUDAS
*Acting Director of the United States Patent and Trademark Office*